US007399782B2

(12) United States Patent
Baden et al.

(10) Patent No.: US 7,399,782 B2
(45) Date of Patent: Jul. 15, 2008

(54) POLYETHER BREVETOXIN DERIVATIVES AS A TREATMENT FOR CYSTIC FIBROSIS, MUCOCILIARY DYSFUNCTION, AND PULMONARY DISEASES

(75) Inventors: Daniel G. Baden, Wilmington, NC (US); William M. Abraham, Miami, FL (US); Andrea J. Bourdelais, Wilmington, NC (US)

(73) Assignee: University of North Carolina at Wilmington, Wilmington, NC (US)

( * ) Notice: Subject to any disclaimer, the term of this patent is extended or adjusted under 35 U.S.C. 154(b) by 390 days.

(21) Appl. No.: 10/945,467

(22) Filed: Sep. 20, 2004

(65) Prior Publication Data

US 2005/0124686 A1 Jun. 9, 2005

Related U.S. Application Data

(60) Provisional application No. 60/504,665, filed on Sep. 19, 2003.

(51) Int. Cl.
*A61K 31/335* (2006.01)

(52) U.S. Cl. .................................................... 514/450

(58) Field of Classification Search ................. 514/450; 549/348

See application file for complete search history.

(56) References Cited

U.S. PATENT DOCUMENTS

| | | | |
|---|---|---|---|
| 4,522,811 | A | 6/1985 | Eppstein et al. |
| 2005/0124685 | A1 | 6/2005 | Baden et al. |
| 2005/0148539 | A1 | 7/2005 | Baden et al. |

FOREIGN PATENT DOCUMENTS

| | | |
|---|---|---|
| WO | WO 03/016353 | 2/2003 |
| WO | WO 2005/027903 | 3/2005 |

OTHER PUBLICATIONS

Abraham et. al., "Airway Responses to Aerosolized Brevetoxins in an animal Model of Asthma", American Journal of Respiratory and Critical Care Medicine, vol. 171, pp. 26-34.*

Boucher, R., "An Overview of the pathogenesis of cystic fibrosis lung disease", Advanced Drug Delivery Reviews 54 (2002), 1359-1371.*

Grant & Grant, Chemical Dictrionary, 5$^{th}$ Edition, p. 147 and 289.*

(Continued)

*Primary Examiner*—Janet L. Andres
*Assistant Examiner*—Binta M Robinson
(74) *Attorney, Agent, or Firm*—McDonnell Boehnen Hulbert & Berghoff

(57) ABSTRACT

Disclosed are compounds that are derivatives of brevetoxin, or PbTx, pharmaceutical formulations comprising the compounds, and methods of regulating mucus transport in a cell, treating mucociliary dysfunction and diseases related to decreased mucus transport, wherein the compounds are of the Formula (I), and Formula (III):

(I)

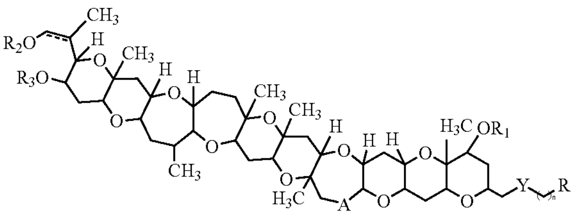

(III)

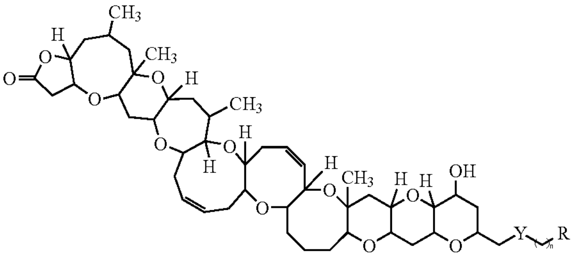

wherein R, $R_1$, $R_2$, $R_3$, A, n, and Y are as defined herein for each compound.

5 Claims, 5 Drawing Sheets

EFFECT OF PbTx ON TMV

OTHER PUBLICATIONS

Grant & Grant, Chemical Dictionary, 5th Edition, p. 147 and 289.*
Alvarez et al., *Chem. Rev.* 1995, 95:1953-1980.
Backer et al., *Harmful Algae*, 2003, 2:19-28.
Baden, *Int. Rev. Cytol.* 1983, 82:99-150.
Baden et al., *Toxicon* 1981, 19(4):455-463.
Baden et al., *Toxicon* 1982, 20(5):929-932.
Baden, *Brevetoxins*, Chemistry, Mechanism of Action, and Methods of Detection, pp. 505-532.
Benson et al., J. of Toxicology and Environ. Health, 1999, 56:345-355.
Berge et al., *J. Pharm. Sci.* 1977, 66(1):1-19.
Bourdelais et al., *Cellular and Molecular Neurogiology* (2004), 24(4):553-563.
Cheng, et al., *Harmful Algae*, 83:1-8.
Dodd et al., *Brain Res.* 1981, 226(1-2):107-18.
Dravid, *Journal of Neurochemistry*, 2004, 89:739-749.
Edwards et al., *Molecular Brain Research*, 1992, 14:64-70.
Gawley et al., *Chemistry & Biology Ltd.* 1995, 2:533-541.
Gould, *Int. J. Pharm.* 1986, 33:201-217.
Hardy et al., *J Neurochem.* 1983, 40(3):608-14.
Jeglitsch, et al., *J. of Pharm. & Experimental Therapeutics*, 1998, 284(2):515-525.
Keck et al., *Tetrahedron Lett.* 1987, 28:139-142.
Kirkpatrick, *Harmful Algae*, 2004, 3:99-115.
Lauredo, et al., *Am J. Physiol Lung Cell Mol Physiol*, 2004, 286:L734-L740.
LePage et al., *Brain Research* 2003, 959(1):120-127.
Liu et al., *Tetrahedron Lett.*, 2000, 56(30):5391-5404.
Mall et al., *Nature Medicine* 2004, 10(5):487-493.
Mende et al., *Tetrahedron Lett.* 1990, 31(37):5307-5310.
Nicolaou et al., *J. Am. Chem. Soc.* 1995, 117:1171.
Poli et al., *Journal of AOAC International* 1995, 78(2):538-42.
Poli et al., *Molecular Pharmacology* 1986, 30:129-135.
Purkerson-Parker et al., 1999, 20(6): 909-920.
Purkerson-Parker et al., *Chemistry & Biology* 2000, 7(6):385-393.
Rein et al., *Journal of Organic Chemistry* 1994, 59(8):2107-13.
Rein et al., *J. Org. Chem.* 1994, 59:2101-2106.
Trainer et al., *Molec. Pharm.* 1991, 40(6):988-994.
Walsh, *Comparative Biochemistry and Physiology Part B*, 2003, 136:173-182.
Washburn, *Toxicon*, 1994, 32(7):799-805.
Wegner, *Current Pharmaceutical Design*, 2001, 7(3):199-212.
Whitney, *Natural Toxins* 1996, 4:261-270.
International Search Report for related PCT Application No. PCT/US2004/030637.
International Search Report for related PCT Application No. PCT/US2004/030665.
International Search Report for related PCT Application No. PCT/US2004/030535.
Alvarez et al., Chem. Rev. 1995, 95:1953-1980.
Backer et al., Harmful Algae, 2003, 2:19-28.
Baden, Int. Rev. Cytol. 1983, 82:99-150.
Baden et al., Toxicon 1981, 19(4):455-463.
Baden et al., Toxicon 1982, 20(5):929-932.
Baden, Brevetoxins, Chem., Mechanism of Action, and Methods of Detection, pp. 505-532.
Benson et al., J. of Toxicology and Environ. Health, 1999, 56:345-355.
Berge et al., J. Pharm. Sci. 1977, 66(1):1-19.
Bourdelais et al., Cellular and Molecular Neurogiology, 2004, 24(4):553-563.
Cheng, et al., Harmful Algae, 83:1-8.
Dodd et al., Brain Res. 1981, 226(1-2):107-18.
Dravid, Journal of Neurochemistry, 2004, 89:739-749.
Edwards et al., Molecular Brain Research, 1992, 14:64-70.
Gawley et al., Chimstry & Biology Ltd., 1995, 2:533-541.
Gould, Int. J. Pharm. 1986, 33:201-217.
Hardy et al., J Neurochem. 1983, 40(3):608-14.
Jeglitsch, et al., J. of Pharm. & Experimental Therapeutics, 1998, 284(2):515-525.
Keck et al., Tetrahedron Lett., 1987, 28:139-142.
Kirkpatrick, Harmful Algae, 2004, 3:99-115.
Lauredo, et al., Am. J. Physiol Lung Cell Mol Physiol, 2004, 286:L734-L740.
LePage et al., Brain Research 2003, 959(1):120-127.
Liu et al., Tetrahedron Lett., 2000, 56(30):5391-5404.
Mall et al., Nature Medicine 2004, 10(5):487-493.
Mende et al., Tetrahedron Lett. 1990, 31(37):5307-5310.
Nicolaou et al., J. Am. Chem. Soc. 1995, 117:1171.
Poli et al., Journal of AOAC International 1995, 78(2):538-42.
Poli et al., Molecular Pharmacology 1986, 30:129-135.
Purkerson-Parker et al., 1999, 20(6):909-920.
Purkerson-Parker et al., Chemistry & Biology 2000, 7(6):385-393.
Rein et al., Journal of Organic Chemistry 1994, 59(8):2107-13.
Rein et al., J. Org. Chem. 1994, 59:2101-2106.
Trainer et al., Molec. Pharm. 1991, 40(6):988-994.
Walsh, Comparative Biochemistry and Physiology Part B, 2003, 136:173-182.
Washburn, Toxicon, 1994, 32(7):799-805.
Wegner, Current Pharmaceutical Design, 2001, 7(3):199-212.
Whitney, Natural Toxins 1996, 4:261-270.

* cited by examiner

Effect of PbTx Antagonist on Airway Responses

POLYETHER BREVETOXIN DERIVATIVES AS A TREATMENT FOR CYSTIC FIBROSIS, MUCOCILIARY DYSFUNCTION, AND PULMONARY DISEASES

CROSS-REFERENCE TO RELATED APPLICATIONS

This application claims priority to U.S. Provisional Application 60/504,665, filed Sep. 19, 2003.

BACKGROUND OF THE INVENTION

1. Field of the Invention

The invention relates to brevetoxin derivative compounds, pharmaceutical formulations comprising the brevetoxin derivatives, and methods of treating diseases that are related to decreased mucus transport using the compounds and pharmaceutical formulations.

2. Description of the Related Art

Decreased mucus transport is characteristic of conditions and diseases such as airway obstruction, asthma, increased incidence of pulmonary disease and/or infection, and cystic fibrosis. In particular, cystic fibrosis is characterized by abnormal functioning of the airway epithelial cells. Cystic fibrosis (or "CF") is caused by a defective gene that codes for a $Na^+/Cl^-$ transporter present on the surface of the epithelial cells that line the trachea, lungs, and other organs, including the intestines, pancreas, reproductive organs, and kidneys. Hundreds of mutations have been identified in this gene, all of which result in defective transport of sodium and chloride by epithelial cells. The severity of the disease symptoms is related to the inherited gene mutation or mutations. These observations indicate that activation of sodium channels can lead to bronchoconstriction and, in some cases, defects in mucus transport, both of which are associated with airway diseases, including CF.

The class of compounds known as the brevetoxins were initially discovered when they were purified as toxins from cultures of the Florida red tide organism *Karenia brevis* also known as *Gymnodinium breve* and *Ptychodiscus brevis* (Baden, D. G., et al., *Toxicon,* 1982; 20(5):929-932). *K. Brevis* proliferates during red tide incidents. The brevetoxins, also known as "PbTx" toxins (Ptychodiscus brevis toxin), have since been characterized and found to be polycyclic-polyethers that initially were shown to have binding activity to a unique site associated with rat brain synaptosomes (Poli, M. A., et al., *Molec. Pharm.,* 1986; 30:129-135). Brevetoxins are classified as neurotoxins that are known to bind to voltage gated sodium channels. In particular, the effects of brevetoxins are mediated by interaction with receptor site 5 on the sodium channels. The general brevetoxin A and brevetoxin B backbone structure are as follows, with PbTx molecules (1-10) described.

Brevetoxin B Backbone

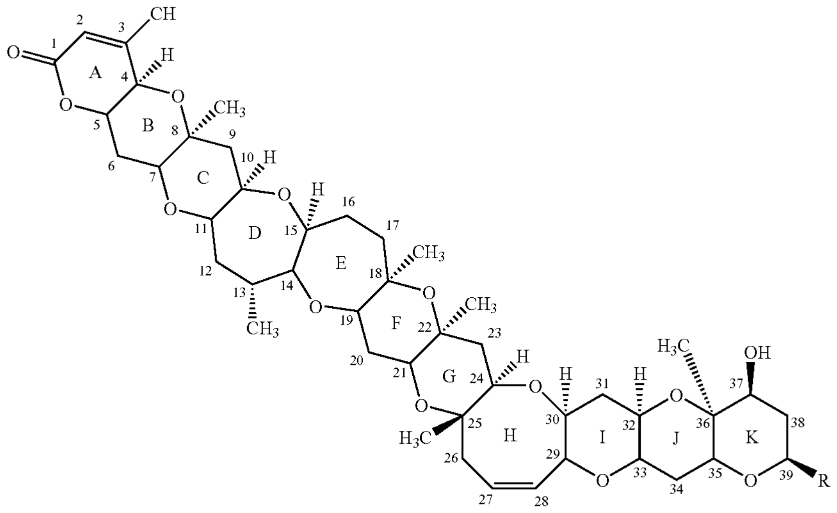

PbTx-2: R is $CH_2C(=CH_2)CHO$;

PbTx-3: R is $CH_2C(=CH_2)CH_2OH$;

PbTx-5: R is $CH_2C(=CH_2)CHO$, and OAc (instead of OH) at C37;

PbTx-6 R is $CH_2C(=CH_2)CHO$, and an epoxide at C27, C28 (instead of double bond);

PbTx-8 R is $CH_2COCH_2Cl$

PbTx-9 R is $CH_2CH(CH_3)CH_2OH$.

Brevetoxin A Backbone

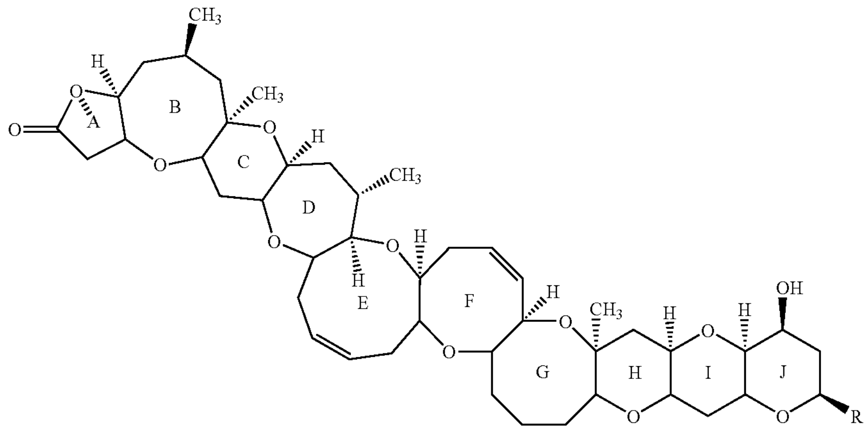

PbTx-1: R is $CH_2C(=CH_2)CHO$;
PbTx-7: R is $CH_2C(=CH_2)CH_2OH$;
PbTx-10 R is $CH_2CH(CH_3)CH_2OH$.

Generally, the activity of brevetoxins is thought to derive from the general backbone structure. Ring A and intact rings H, I, J, and K have been reported to be essential for the toxic activity of these compounds. There have been no reports that link toxic activity of brevetoxins to the various side chains appended to the backbone structure.

β-Naphthoyl-PbTx-3 is a brevetoxin derivative that reduces sodium channel openings and effectively antagonizes the actions of the native toxin in channel activation (Purkerson-Parker, Chemistry and Biology, 2000; 7(6):385-393). β-Naphthoyl-PbTx-3 is thought to displace the native toxin from its binding site, does not elicit opening of sodium channels in the steady state, and findings indicate that it blocks brevetoxin-induced opening of sodium channels.

If activation of voltage gated sodium channels causes airway related diseases or conditions, effective modulation or blockade of voltage gated sodium channels can be useful in alleviating airway pathologies associated with mucociliary dysfunction, such as asthma, chronic obstructive pulmonary diseases, pulmonary infection (e.g., pneumonia, *Pseudomonas*), and cystic fibrosis. Thus, there is a need for active agents that can act at the CFTR, $P2Y_2$ receptors, $A_2B$ receptors, purinergic receptors, and chloride ion channels, binding to voltage gated sodium channels, which are useful in the regulation of mucus transport, as well as treatment or prevention of conditions or diseases associated with decreased mucus transport.

SUMMARY OF THE INVENTION

The invention provides compounds, or pharmaceutically acceptable salts, solvates, hydrates, complexes, or combinations thereof, of Formula (I):

(I)

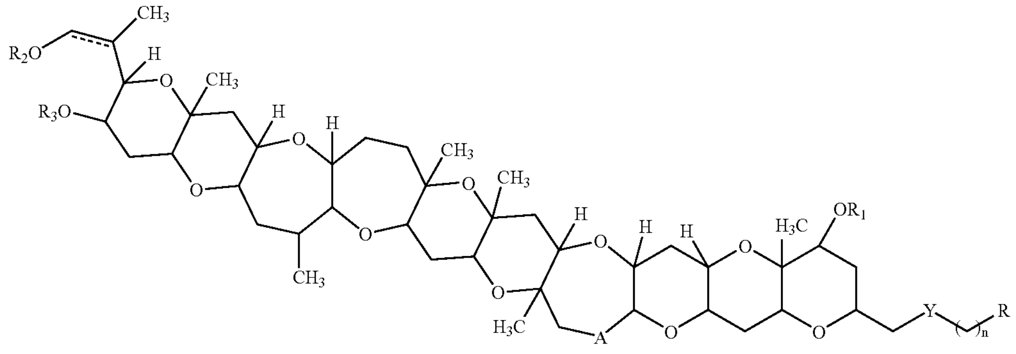

wherein

A is

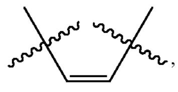

, 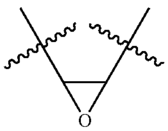

, or

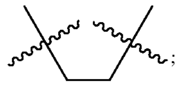

;

R is $C_1$-$C_6$ alkyl, $C_2$-$C_6$ alkenyl, $C_3$-$C_8$ cycloalkylcarbonyl, $C_1$-$C_6$ alkyl ester, $C_2$-$C_6$ alkenyl ester, amino, amido, aryl ester, cycloalkyl ester, cycloalkenyl ester, purinyl, pyrimidinyl, heterocyclyl, aryl, or heteroaryl, each of which is optionally substituted on any available carbon atom with $C_1$-$C_{10}$ alkyl, $C_3$-$C_8$ cycloalkyl, $C_3$-$C_8$ cycloalkyl($C_1$-$C_6$) alkyl, $C_3$-$C_8$ cycloalkyl($C_1$-$C_6$)alkoxy, $C_1$-$C_{10}$ alkoxy, halogen, hydroxy, cyano, nitro, amino, mono($C_1$-$C_6$)alkylamino, di($C_1$-$C_6$)alkylamino, $C_2$-$C_{10}$alkenyl, $C_2$-$C_{10}$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl;

$R_1$ is H or —(CO)$CH_3$; and $R_2$ and $R_3$ at each occurrence are independently —$CH_2$(CO)$CH_3$, —$CH_2$(CO)$CH_2CH_3$, —$CH_2$(CO)$CH(CH_3)_2$, —$CH_2$(CO)$CH_2CH_2CH_3$, —$CH_2$(CO)$CH(CH_3)CH_2CH_3$, or —$CH_2$(CO)$CH_2CH(CH_3)_2$, or $OR_2$ and $OR_3$ can be taken together to form a six membered ring of the formula (Ia)

and when n is 1, R is not:

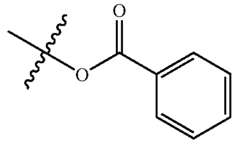,
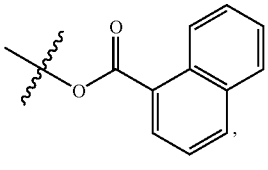, or
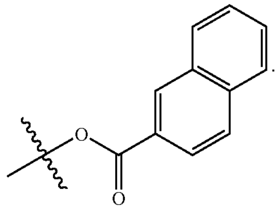.

The invention also provides compounds, or pharmaceutically acceptable salts, solvates, hydrates, complexes, or combinations thereof, of the Formula (II):

(II)

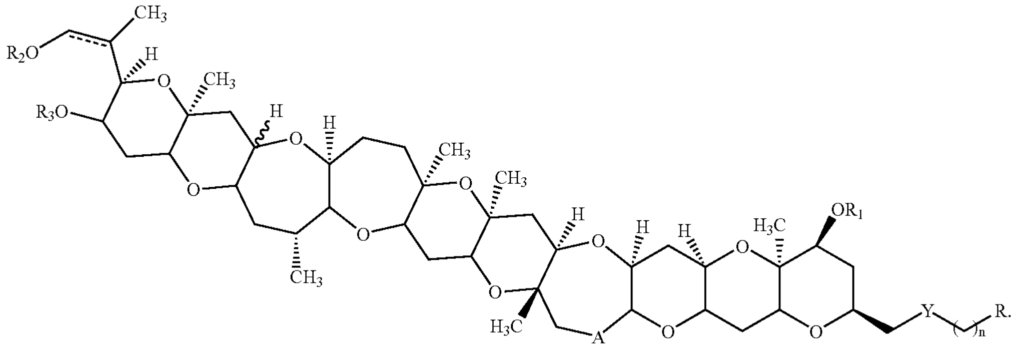

(Ia)

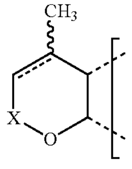

wherein X is C═O, $CH_2$, or $CH(CH_3)$;

wherein the bracketed-dashed bonds indicate attachment to backbone;

Y is CH═CH, C(O), $CH(CH_3)$, or $CH_2$; and n is 1 or 0; and with the proviso that when $OR_2$ and $OR_3$ are taken together to form a ring of the formula (Ia), wherein X is C═O and the double bond is present; when A is

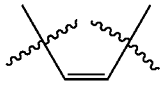;

wherein

A is

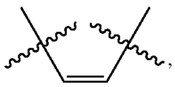,
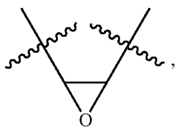, or
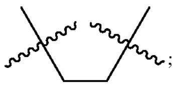;

R is $C_1$-$C_6$ alkyl, $C_2$-$C_6$ alkenyl, $C_1$-$C_6$ alkyl ester, $C_2$-$C_6$ alkenyl ester, amino, amido, aryl ester, cycloalkyl ester, cycloalkenyl ester, purinyl, pyrimidinyl, heterocyclyl, aryl, or heteroaryl;

$R_1$ is H or —$COCH_3$; and $R_2$ and $R_3$ at each occurrence are independently —$CH_2COCH_3$, —$CH_2COCH_2CH_3$, —$CH_2COCH(CH_3)_2$, —$CH_2COCH_2CH_2CH_3$, —$CH_2COCH(CH_3)CH_2CH_3$, or —$CH_2COCH_2CH(CH_3)_2$, or $OR_2$ and $OR_3$ can be taken together to form a six membered ring of the formula (Ia)

(Ia)

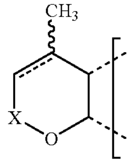

wherein X is C═O or $CH(CH_3)$;

wherein the bracketed-dashed bonds indicate attachment to backbone;

Y is CH═CH, C═O, or $CH_2$; and n is 1 or 0; and with the proviso that when $OR_2$ and $OR_3$ are taken together to form a ring of the formula (Ia), wherein X is C═O and the double bond is present; when A is

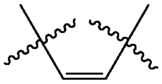
;

and when n is 1, R is not:

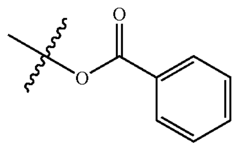
,
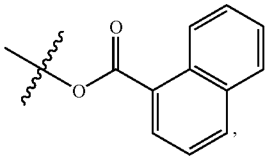
, or
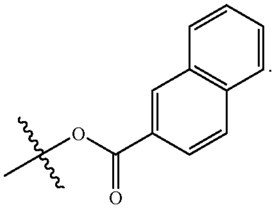
.

Further, the invention provides compounds, or pharmaceutically acceptable salts, solvates, hydrates, complexes, or combinations thereof, of the Formula (III):

(III)

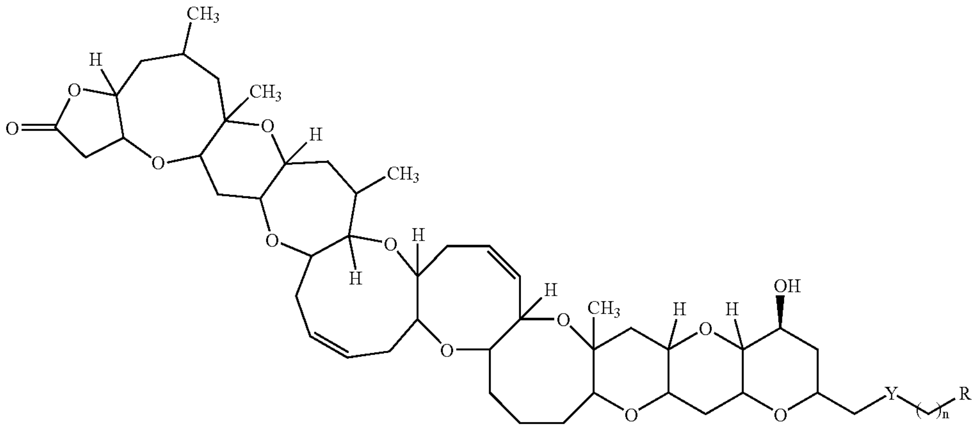

wherein

R is H, OH, halogen, $C_1$-$C_6$ lower alkyl, $C_1$-$C_6$ alkyl esters, $C_2$-$C_6$ alkenyl ester, amino, amido, aldehydo such as formyl, aryl ester, cycloalkyl ester, cycloalkenyl ester, purinyl, pyrimidinyl, heterocyclyl, aryl, or heteroaryl;

n is 1 or 0; and

Y is C═O, CH═CH, $CHCH_3$ or $CH_2$.

Yet further, the instant invention provides compounds, or pharmaceutically acceptable salts, solvates, hydrates, complexes, or combinations thereof, of the Formula (IV):

(IV)

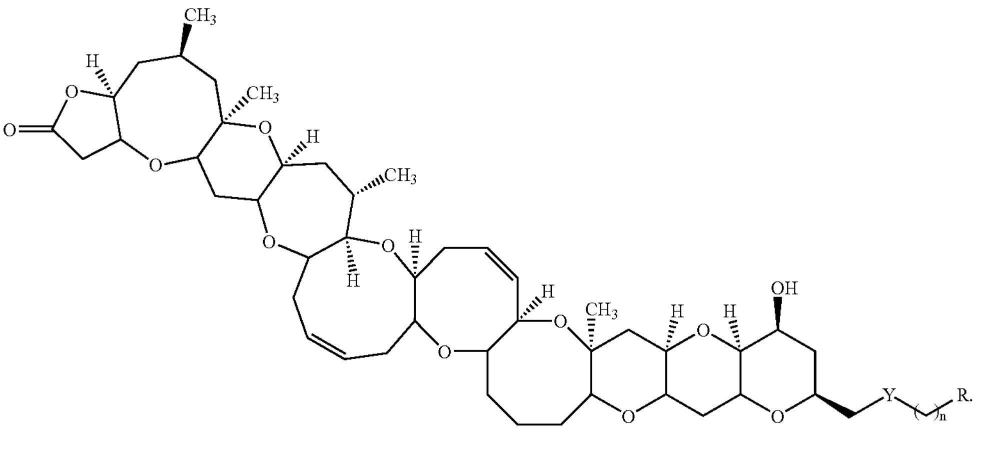

wherein

R is H, OH, halogen, $C_1$-$C_6$ lower alkyl, $C_1$-$C_6$ alkyl ester, $C_2$-$C_6$ alkenyl ester, amino, amido, aldehyde, aryl ester, cycloalkyl ester, cycloalkenyl ester, purinyl, pyrimidinyl, heterocyclyl, aryl, or heteroaryl;

n is 1 or 0; and

Y is CH═CH, C═O, $CH(CH_3)$, or $CH_2$.

The invention also provides pharmaceutical formulations comprising a compound, or a pharmaceutically acceptable salt, solvate, hydrate, complex, or combinations thereof, of Formulas (I), (II), (III), and (IV) in combination with a pharmaceutically acceptable carrier, excipient, solvent, adjuvant or diluent.

The invention further relates to methods of regulating mucus transport velocity and treating conditions or diseases associated with decreased mucus transport or mucociliary dysfunction in a subject comprising administering to a subject a compound of Formula (I), (II), (III), or (IV), or pharmaceutically acceptable salt, solvate, hydrate, complex, or combination thereof.

DETAILED DESCRIPTION OF THE INVENTION

Definitions

Figure 1:
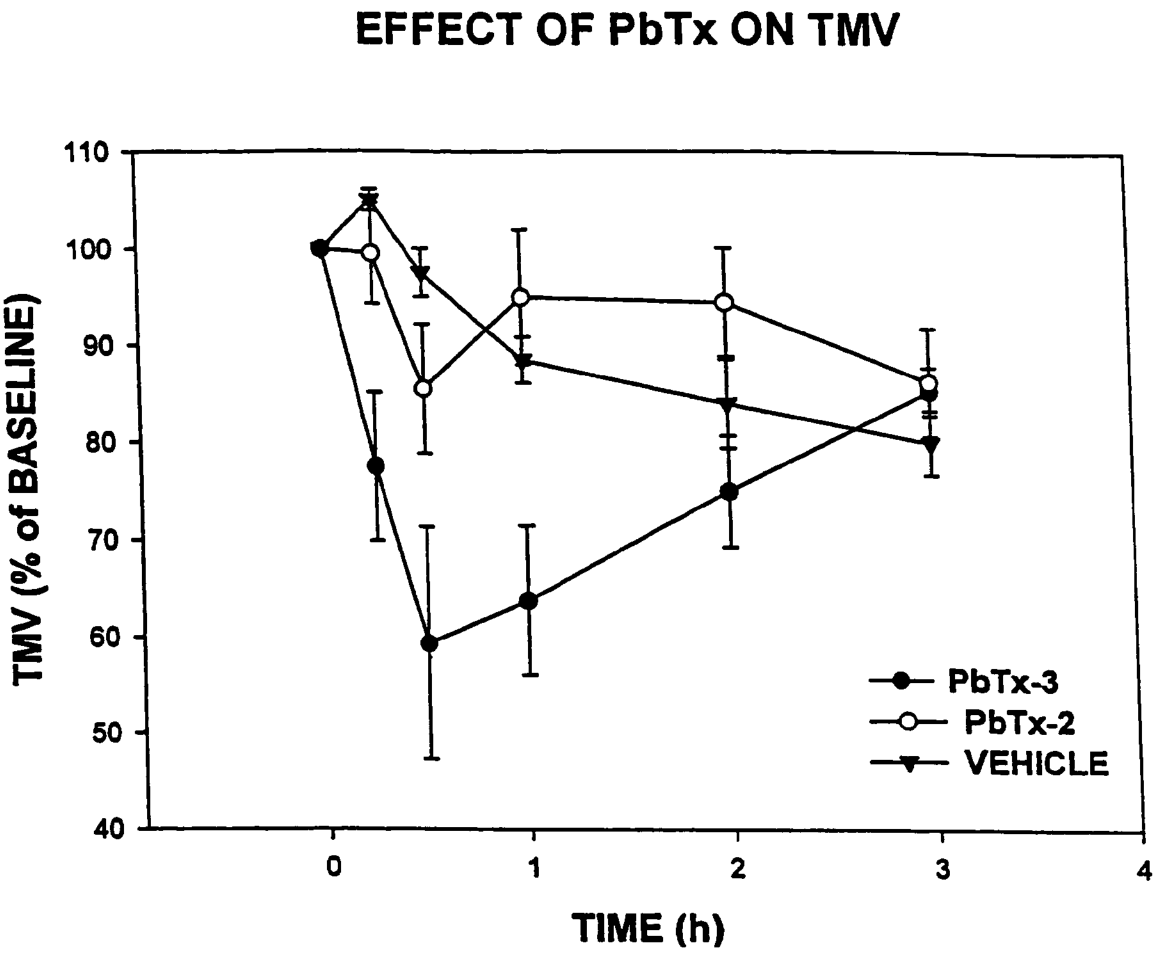
FIG. 1 illustrates the effects of PbTx-2 and PbTx-3 on tracheal mucus velocity (TMV) in conscious allergic sheep, relative to control (vehicle). PbTx-2 was relatively inactive, but PbTx-3 caused a rapid and pronounced decrease in TMV which was sustained for up to 2 h. Values are mean±sem.
Figure 2:
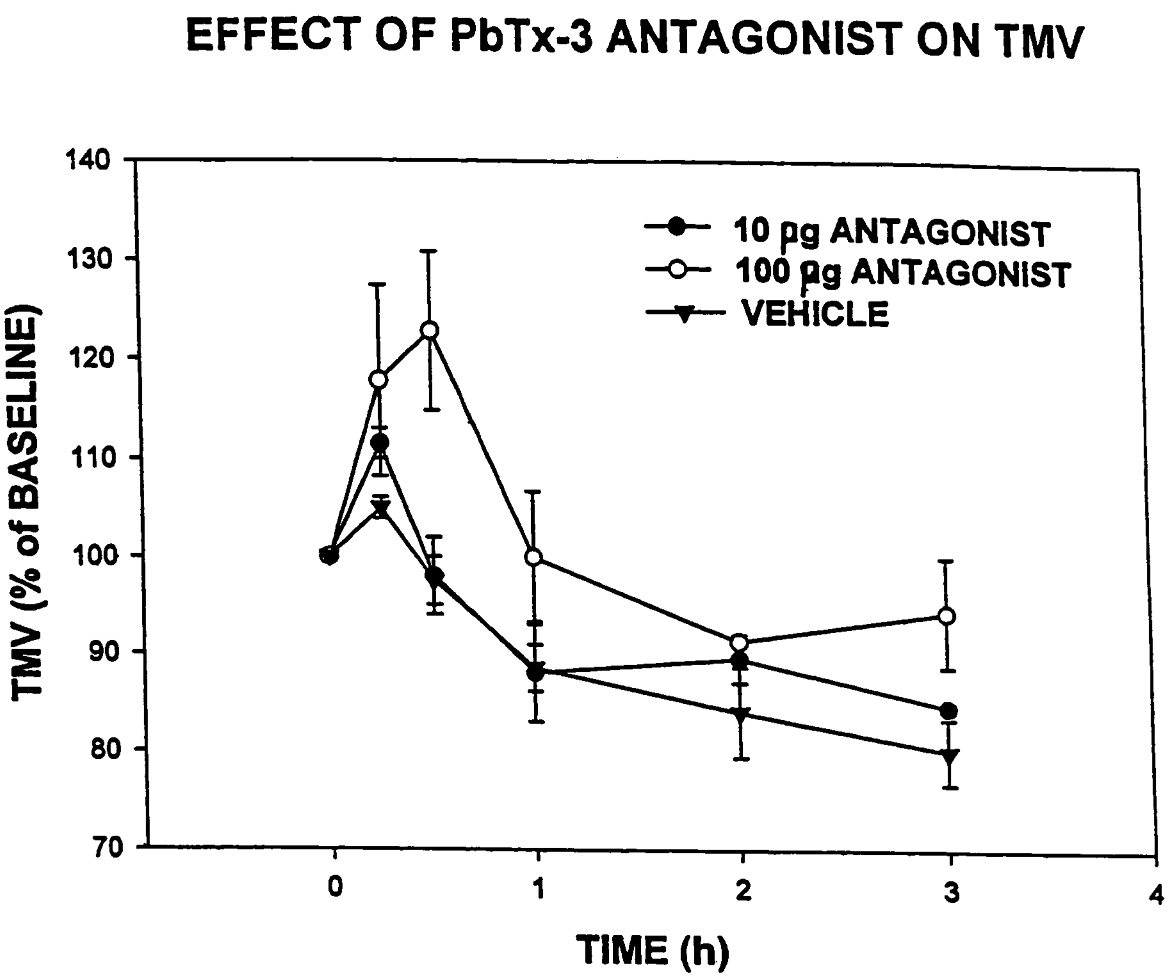
FIG. 2 illustrates the effect of the β-naphthoyl-PbTx-3 derivative on tracheal mucus velocity (TMV) in conscious sheep at 10 pg and 100 pg doses. The effect of the β-naphthoyl derivative at 10 pg (n=2) was about the same as control (vehicle). At 100 pg, (n=4) the β-naphthoyl derivative is able to rapidly increase TMV that is sustainable for about 1 h. Values are mean±se.
Figure 3:
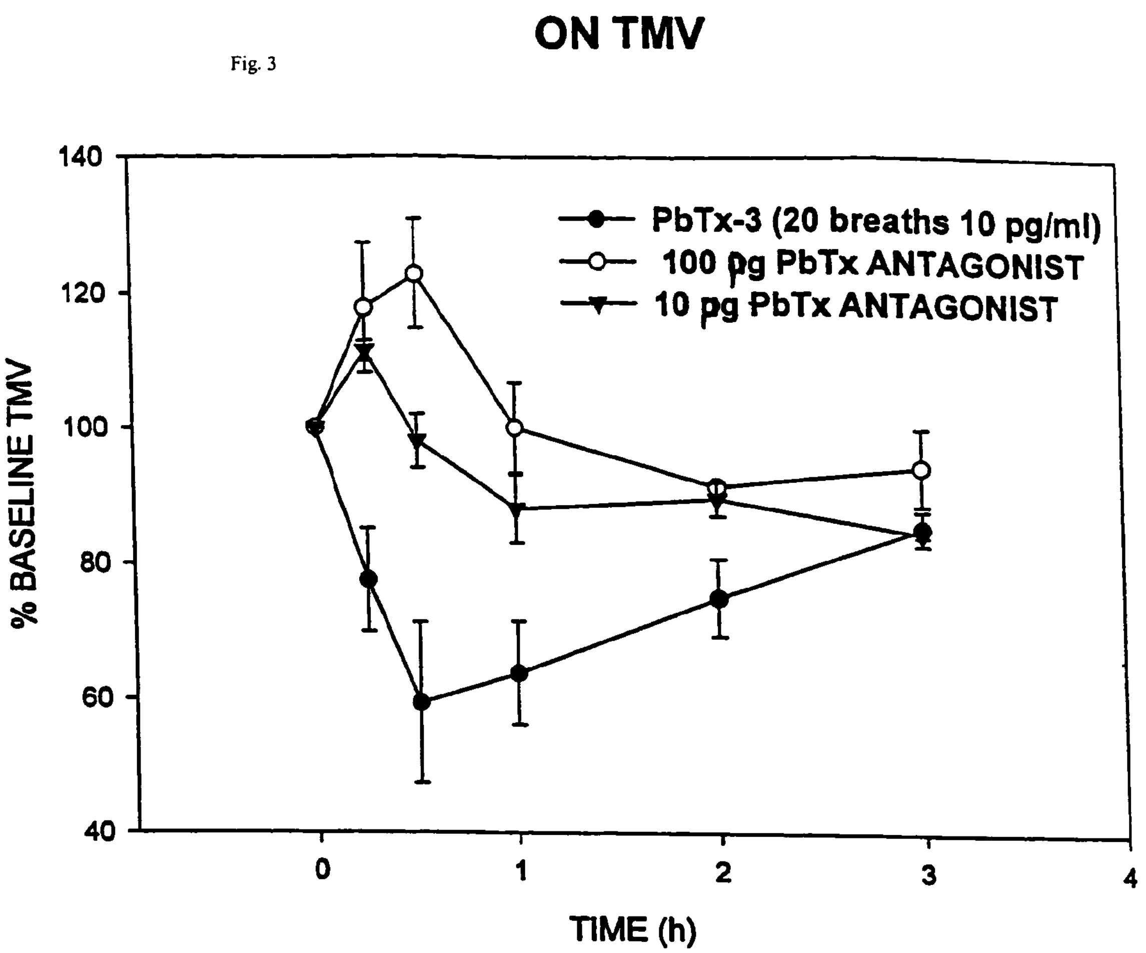
FIG. 3 illustrates the differential effects of PbTx-3 (20 breaths of 10 pg/mL, n=4) and 10 pg (n=2) and 100 pg (n=4) doses of the β-naphthoyl-PbTx-3 antagonist on tracheal mucus velocity in conscious sheep. Values are mean±sem. Administration of the β-naphthoyl-PbTx-3 antagonist at each dosage increased TMV relative to PbTx-3. Values are mean±sem.
Figure 4:
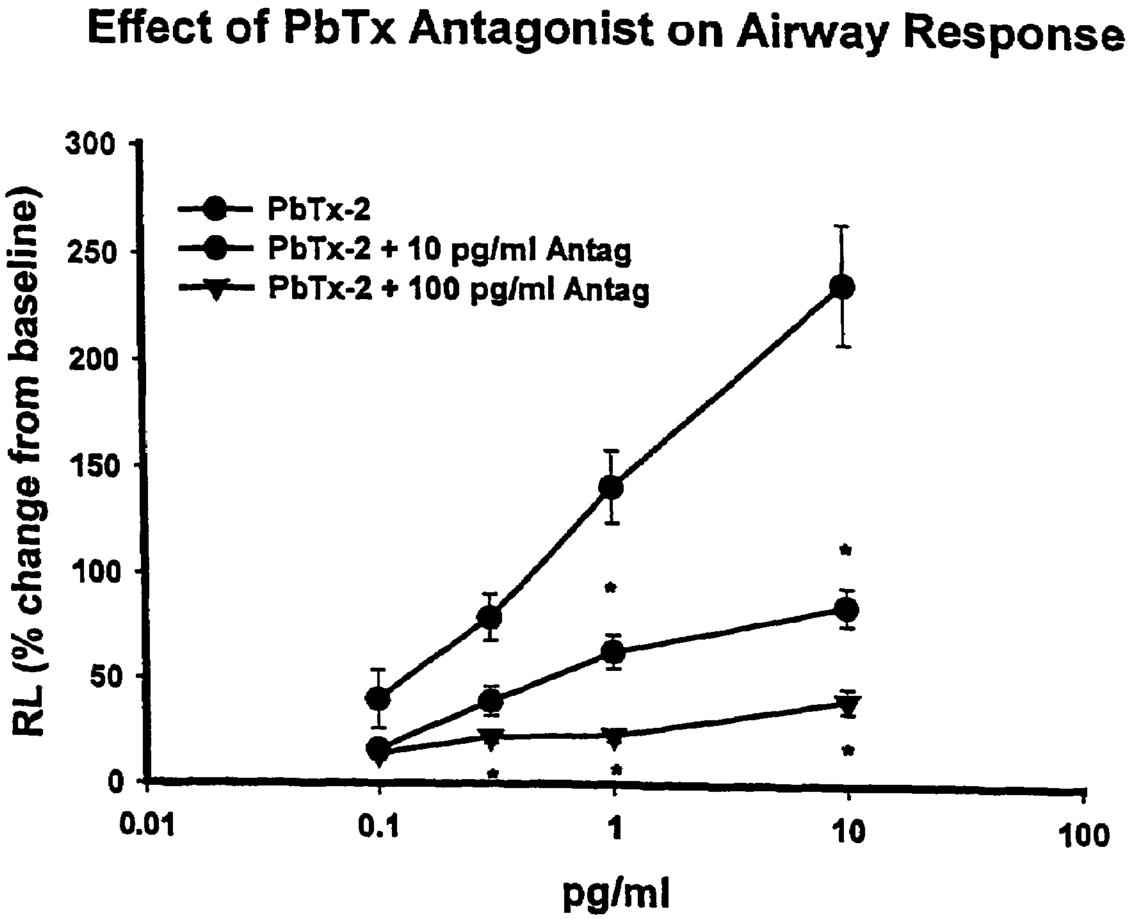
FIG. 4 illustrates the effect of the β-naphthoyl-PbTx-3 derivative on PbTx-2-induced bronchoconstriction in conscious sheep. Twenty breaths of increasing doses of PbTx-2 produced an increase in pulmonary airflow resistance (RL). Pretreating the animals with 20 breaths of 10 pg/mL of β-naphthoyl-PbTx-3 at 15 minutes prior to PbTx-2 challenge blocked PbTx-2-induced bronchoconstriction. Values are mean±sem for 4-6 sheep.
Figure 5:
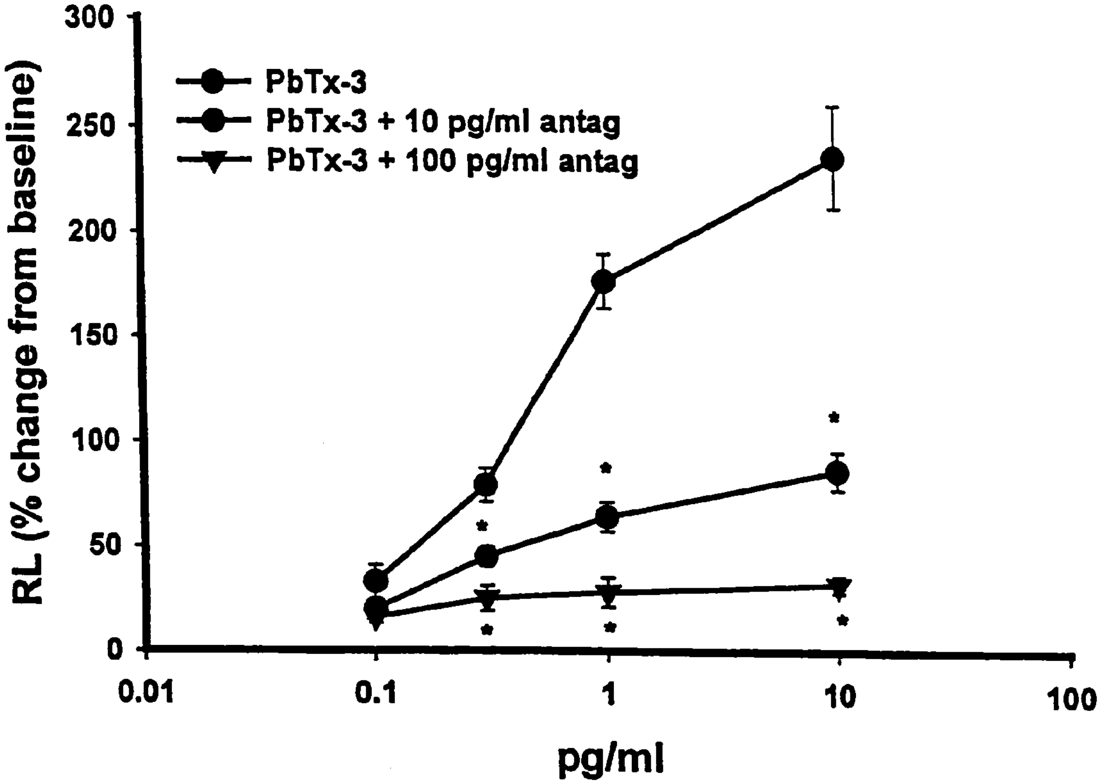
FIG. 5 illustrates the effect of the β-naphthoyl-PbTx-3 derivative on PbTx-3-induced bronchoconstriction in conscious sheep. Twenty breaths of increasing doses of PbTx-3 produced an increase in pulmonary airflow resistance (RL). Pretreating the animals with 20 breaths of 10 pg/mL of β-naphthoyl-PbTx-3 at 15 minutes prior to PbTx-3 challenge blocked PbTx-3-induced constrictor response. Pretreatment of the animals with 20 breaths of 100 pg/mL β-naphthoyl-PbTx-3 at 15 minutes prior to PbTx-3 challenge, provided an increase the inhibition of PbTx-3-induced bronchoconstriction. Values are mean±sem for 4-6 sheep.

Unless defined otherwise, all scientific and technical terms used herein have the same meaning as commonly understood by one of skill in the art to which this invention belongs.

All patents and publications referred to herein are hereby incorporated by reference for all purposes.

A "therapeutically effective" amount is defined as an amount effective to reduce or lessen at least one symptom of the disease being treated or to reduce or delay onset of one or more clinical markers or symptoms of the disease.

As used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

By "alkyl" and "$C_1$-$C_6$ alkyl" is meant straight or branched chain alkyl groups having 1-6 carbon atoms, such as, methyl, ethyl, propyl, isopropyl, n-butyl, sec-butyl, tert-butyl, pentyl, 2-pentyl, isopentyl, neopentyl, hexyl, 2-hexyl, 3-hexyl, and 3-methylpentyl. It is understood that in cases where an alkyl chain of a substituent (e.g. of an alkyl, alkoxy or alkenyl group) is shorter or longer than 6 carbons, it will be so indicated in the second "C" as, for example, "$C_1$-$C_{10}$" indicates a maximum of 10 carbons. The alkyl groups herein are optionally substituted in one or more substitutable positions with various groups.

By the term "halogen" is meant fluorine, bromine, chlorine, and iodine.

"Alkenyl" and "$C_2$-$C_6$ alkenyl" means straight and branched hydrocarbon groups having from 2 to 6 carbon atoms and from one to three double bonds and includes, for example, ethenyl, propenyl, 1-but-3-enyl, 1-pent-3-enyl, 1-hex-5-enyl and the like. The alkenyl groups herein are optionally substituted in one or more substitutable positions with various groups.

As used herein, the term "cycloalkyl" refers to saturated carbocyclic groups having three to twelve carbon atoms. The cycloalkyl can be monocyclic, or a polycyclic fused system. Examples of such groups include cyclopropyl, cyclobutyl, cyclopentyl and cyclohexyl. The cycloalkyl groups herein are unsubstituted or, as specified, substituted in one or more substitutable positions with various groups. For example, such cycloalkyl groups may be optionally substituted with, for example, $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "aryl" is meant an aromatic carbocyclic group having a single ring (e.g., phenyl), multiple rings (e.g., biphenyl), or multiple condensed rings in which at least one is aromatic, (e.g., 1,2,3,4-tetrahydronaphthyl, naphthyl), which is optionally mono-, di-, or trisubstituted. Preferred aryl groups of the invention are phenyl, 1-naphthyl, 2-naphthyl, indanyl, indenyl, dihydronaphthyl, tetralinyl or 6,7,8,9-tetrahydro-5H-benzo[α]cycloheptenyl. The aryl groups herein are unsubstituted or, as specified, substituted in one or more substitutable positions with various groups. Preferred aryl groups are optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

As used herein, the term "arylester" encompasses aryloxycarbonyl and arylcarbonyloxy groups.

As used herein, the term "alkylester" encompasses alkyloxycarbonyl and alkylcarbonyloxy groups. As used herein, alkylcarbonyl carries the same meaning as alkanoyl.

As used herein, the term "alkylamide" encompasses alkylaminocarbonyl groups, dialkylcarbonyl groups, and alkanoylamino groups.

As used herein, the term "alkenylamide" encompasses alkenylaminocarbonyl groups, dialkenylcarbonyl groups, and alkenylcarbonylamino groups.

As used herein, the term "alkenylester" encompasses alkenyloxycarbonyl and alkenylcarbonyloxy groups.

The term alkylarylester as used herein refers to alkyloxycarbonyl and akanoyloxy groups in which the alkyl portion carries an aryl or heteroaryl group.

The term alkenylarylester as used herein refers to alkenyloxycarbonyl and alkenylcarbonyloxy groups in which the alkenyl portion carries an aryl or heteroaryl group.

By "heteroaryl" is meant one or more aromatic ring systems of 5-, 6-, or 7-membered rings which includes fused ring systems of 9-11 atoms containing at least one and up to four heteroatoms selected from nitrogen, oxygen, or sulfur. Preferred heteroaryl groups of the invention include pyridinyl, pyrimidinyl, quinolinyl, benzothienyl, indolyl, indolinyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thiazolyl, indolizinyl, indazolyl, benzothiazolyl, benzimidazolyl, benzofuranyl, furanyl, thienyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromonyl, chromanonyl, pyridinyl-N-oxide, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide, benzothiopyranyl S,S-dioxide. The heteroaryl groups herein are unsubstituted or, as specified, substituted in one or more substitutable positions with various groups. Preferred heteroaryl groups are optionally substituted with $C_1$-$C_6$ alkyl, $C_1$-$C_6$ alkoxy, halogen, hydroxy, cyano, nitro, amino, mono ($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

By "heterocycle", "heterocycloalkyl" or "heterocyclyl" is meant one or more carbocyclic ring systems of 4-, 5-, 6-, or 7-membered rings which includes fused ring systems of 9-11 atoms containing at least one and up to four heteroatoms selected from nitrogen, oxygen, or sulfur. Preferred heterocycles of the invention include morpholinyl, thiomorpholinyl, thiomorpholinyl S-oxide, thiomorpholinyl S,S-dioxide, piperazinyl, homopiperazinyl, pyrrolidinyl, pyrrolinyl, tetrahydropyranyl, piperidinyl, tetrahydrofuranyl, tetrahydrothienyl, homopiperidinyl, homomorpholinyl, homothiomorpholinyl, homothiomorpholinyl S,S-dioxide, oxazolidinonyl, dihydropyrazolyl, dihydropyrrolyl, dihydropyrazinyl, dihydropyridinyl, dihydropyrimidinyl, dihydrofuryl, dihydropyranyl, tetrahydrothienyl S-oxide, tetrahydrothienyl S,S-dioxide and homothiomorpholinyl S-oxide. The heterocycle groups herein are unsubstituted or, as specified, substituted in one or more substitutable positions with various groups. Preferred heterocycle groups are optionally substituted with $C_1$-$C_6$ alkyl, $C_1$-$C_6$ alkoxy, halogen, hydroxy, cyano, nitro, amino, mono($C_1$-$C_6$)alkylamino, di($C_1$-$C_6$)alkylamino, $C_2$-$C_6$alkenyl, $C_2$-$C_6$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl, di($C_1$-$C_6$)alkylamino($C_1$-$C_6$) alkyl or =O.

The phrase "regulating mucus clearance" encompasses controlling, promoting and/or influencing mucus clearance.

As used herein, the terms "treatment" and "treating" encompass prophylactic administration of the compound or a pharmaceutical composition comprising the compound ("prophylaxis") as well as remedial therapy to reduce or eliminate a disease or disorder mentioned herein. Prophylactic administration is intended for preventing disorders or preventing recurrence of disorders and may be used to treat a subject that is at risk of having or suffering from one or more disorders mentioned herein. Thus, as used herein, the term "treatment", or a derivative thereof, contemplates partial or complete inhibition of the stated disease state, when an active ingredient of the invention is administered prophylactically or following the onset of the disease state for which such active ingredient of the is administered. "Prophylaxis" refers to administration of the active ingredient(s) to a mammal to protect the mammal from any of the disorders set forth herein, as well as others.

As used herein, the term "subject" encompasses animals, including mammals and fish. Preferably the term refers to mammals such as a humans, cattle and horses, more preferably to humans and domestic animals such as cats, dogs, and horses, and most preferably to humans.

Preferred compounds of the invention include those where $R_1$ is hydrogen, A is

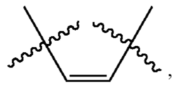, $OR_2$ and $OR_3$ represent a ring of formula (Ia)

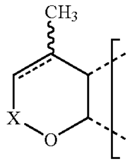

(Ia) where X is C=O;

Y is CH=CH, and R is substituted benzoyl or substituted naphthoyl. These compounds are hereinafter referred to as compounds of Formula A-1.

In compounds of Formula A-1, each benzoyl and naphthoyl is substituted with from 1-5 independently selected $R_b$ groups. Preferred $R_b$ groups on benzoyl and naphthoyl include $C_1$-$C_{10}$ alkyl, $C_3$-$C_8$ cycloalkyl, $C_3$-$C_8$ cycloalkyl($C_1$-$C_6$)alkyl, $C_3$-$C_8$ cycloalkyl($C_1$-$C_6$)alkoxy, $C_1$-$C_{10}$ alkoxy, halogen, hydroxy, cyano, nitro, amino, mono($C_1$-$C_6$)alkylamino, di($C_1$-$C_6$)alkylamino, $C_2$-$C_{10}$alkenyl, $C_2$-$C_{10}$alkynyl, $C_1$-$C_6$ haloalkyl, $C_1$-$C_6$ haloalkoxy, amino ($C_1$-$C_6$)alkyl, mono($C_1$-$C_6$)alkylamino($C_1$-$C_6$)alkyl or di($C_1$-$C_6$)alkylamino($C_1$-$C_6$)alkyl.

Or, any two adjacent $R_b$ groups together with the atoms to which they are attached form a partially saturated 5-8 membered ring, where the 5-8 membered ring is optionally substituted with from 1 to 3 of $R_e$, where each $R_e$ is $C_1$-$C_{10}$ alkyl, $C_3$-$C_8$ cycloalkyl, $C_3$-$C_8$ cycloalkyl($C_1$-$C_6$)alkyl, $C_3$-$C_8$ cycloalkyl($C_1$-$C_6$) alkoxy, $C_1$-$C_{10}$ alkoxy, halogen, hydroxy, cyano, nitro, amino, mono($C_1$-$C_6$)alkylamino, di($C_1$-$C_6$)alkylamino, $C_2$-$C_{10}$alkenyl, $C_2$-$C_{10}$alkynyl, $C_1$-$C_6$ haloalkyl, $C_1$-$C_6$ haloalkoxy, amino($C_1$-$C_6$)alkyl, mono($C_1$-$C_6$)alkylamino($C_1$-$C_6$)alkyl or di($C_1$-$C_6$)alkylamino($C_1$-$C_6$) alkyl.

Preferably, R is benzoyl or naphthoyl, each of which is substituted with 1-3 of $R_b$, where each $R_b$ is independently $C_1$-$C_{10}$ alkyl, $C_3$-$C_8$ cycloalkyl, $C_3$-$C_8$ cycloalkyl($C_1$-$C_6$) alkyl, $C_3$-$C_8$ cycloalkyl($C_1$-$C_6$)alkoxy, $C_1$-$C_{10}$ alkoxy, halogen, mono($C_1$-$C_6$)alkylamino, di($C_1$-$C_6$)alkylamino, $C_2$-$C_{10}$alkenyl, $C_2$-$C_{10}$alkynyl, $C_1$-$C_6$ haloalkyl, $C_1$-$C_6$ haloalkoxy, mono($C_1$-$C_6$)alkylamino($C_1$-$C_6$)alkyl or di($C_1$-$C_6$)alkylamino($C_1$-$C_6$)alkyl.

More preferably, R is benzoyl or naphthoyl, each of which is substituted with 1-2 of $R_b$, where each $R_b$ is independently $C_1$-$C_{10}$ alkyl, $C_3$-$C_8$ cycloalkyl, $C_3$-$C_8$ cycloalkyl($C_1$-$C_6$) alkyl, $C_3$-$C_8$ cycloalkyl($C_1$-$C_6$)alkoxy, $C_2$-$C_{10}$alkenyl, or $C_2$-$C_{10}$alkynyl.

In one aspect, the invention relates to compounds of Formula (I):

$R_2$ and $R_3$ at each occurrence are independently $-CH_2(CO)CH_3$, $-CH_2(CO)CH_2CH_3$, $-CH_2(CO)CH(CH_3)_2$, $-CH_2(CO)CH_2CH_2CH_3$, $-CH_2(CO)CH(CH_3)CH_2CH_3$, or $-CH_2(CO)CH_2CH(CH_3)_2$, or $OR_2$ and $OR_3$ can be taken together to form a six membered ring of the formula (Ia)

(Ia)

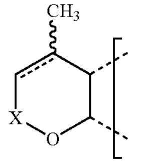

wherein X is C═O or $CH(CH_3)$;

wherein the bracketed-dashed bonds indicate attachment to backbone; and

Y is CH═CH, C═O, $CHCH_3$, or $CH_2$;

n is 1 or 0; and (I)

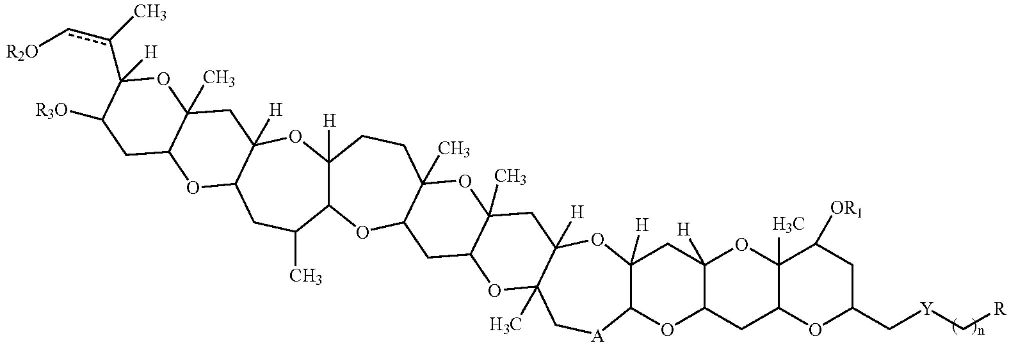

wherein

A is

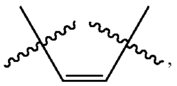

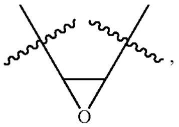

or

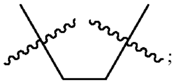

R is $C_1$-$C_6$ alkyl, $C_2$-$C_6$ alkenyl, $C_1$-$C_6$ alkyl esters, $C_2$-$C_6$ alkenyl esters, amines, amides, aryl esters, cycloalkyl esters, cycloalkenyl esters, purines, pyrimidines, heterocycle, or heteroaryl;

$R_1$ is H or $-(CO)CH_3$; and with the proviso that when $OR_2$ and $OR_3$ are taken together to form a ring of the formula (Ia), wherein X is C═O and the double bond is present; when A is

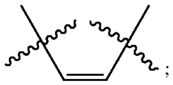

and when n is 1, R is not:

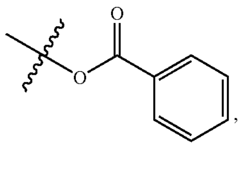

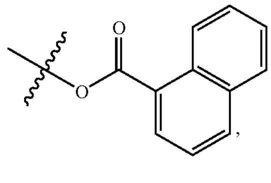

or

-continued

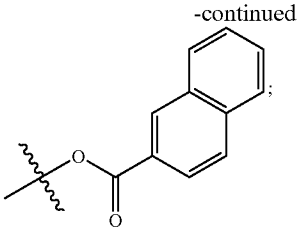

or a pharmaceutically acceptable salt, solvate, hydrate, complex, or combination thereof.

In a broad aspect, R is alkyl, alkyl ester, halogen, alkenyl, alkenyl ester, cycloalkyl, cycloalkyl ester, aryl, aryl ester, heteroaryl, heterocycle, heterocycloalkyl or heterocyclyl.

In another embodiment of this aspect, the compound is of Formula (I), wherein R is

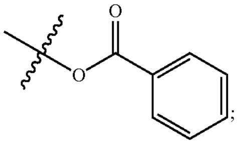
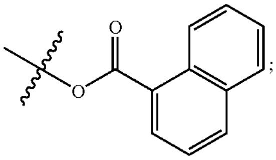
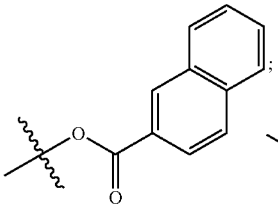
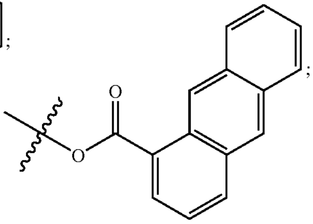
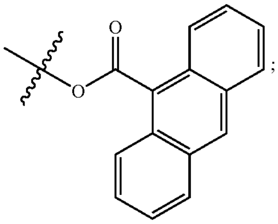
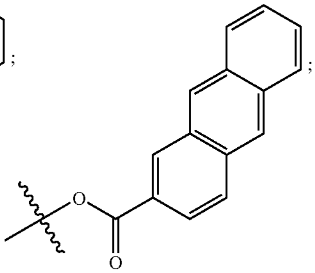
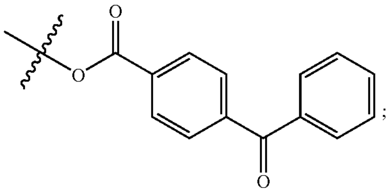
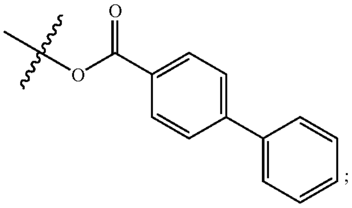

-continued

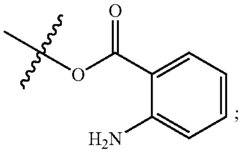
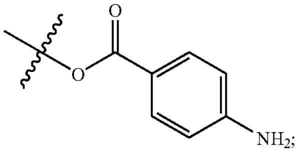
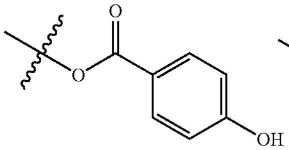
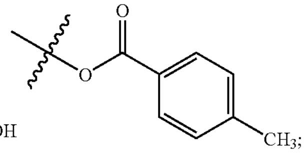
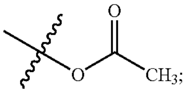
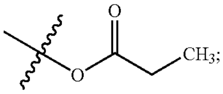
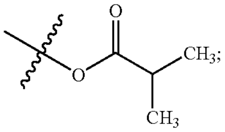
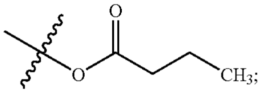
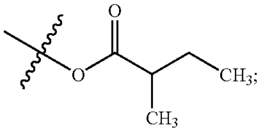
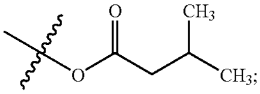
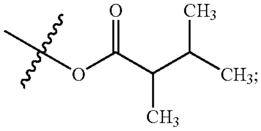
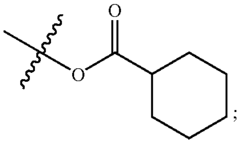
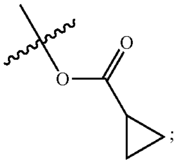
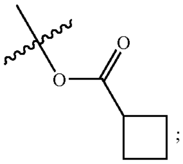
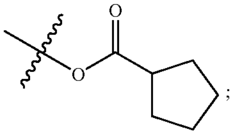
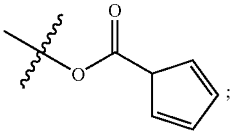
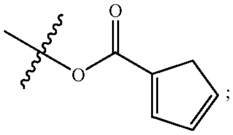
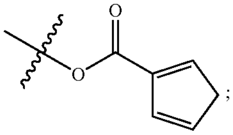
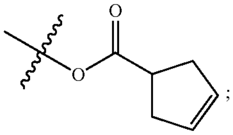
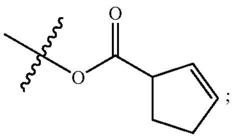

-continued

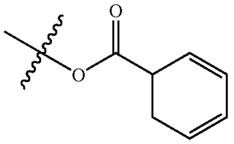
;
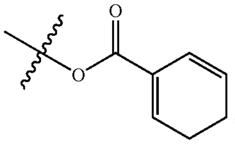
;
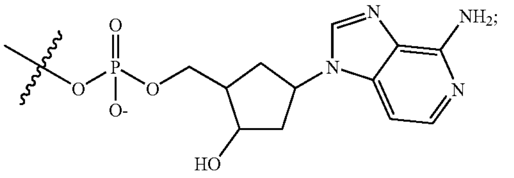

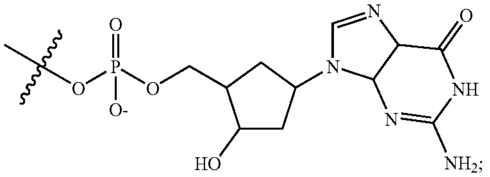

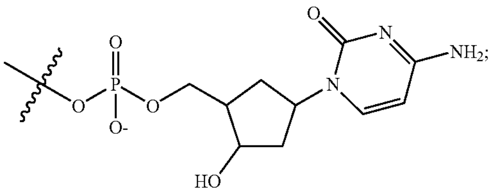

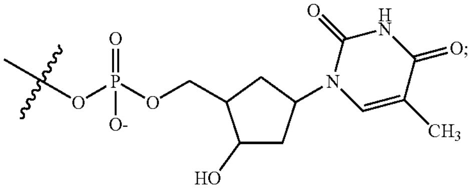

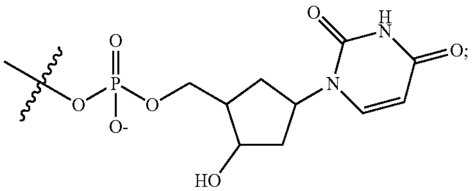

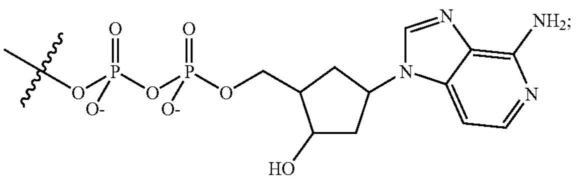

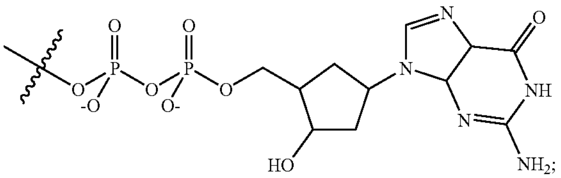

-continued

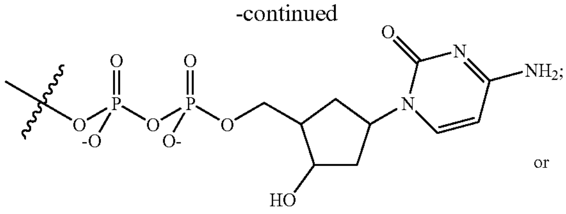
or
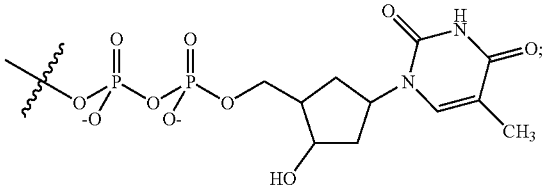

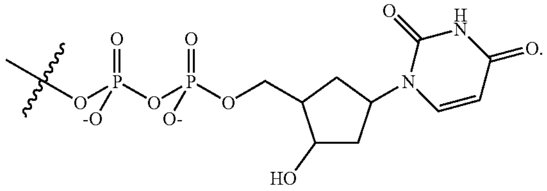

In a further embodiment of this aspect, the compound is of Formula (I), wherein R is benzoyl, α-naphthoyl, β-naphthoyl, α-anthracoyl, β-anthracoyl, or γ-anthracoyl.

In another embodiment of this aspect, $OR_2$ and $OR_3$ are taken together to form a ring of formula (Ia), wherein the ring is

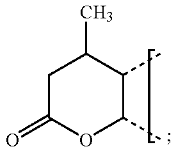

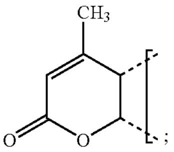

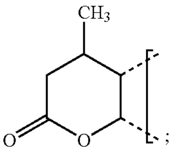

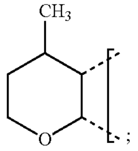
or
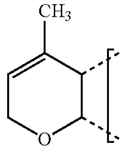

wherein the bracketed-dashed bonds indicate the point of attachment to the backbone.

In even another embodiment of this aspect, $R_2$ and $R_3$ are each independently

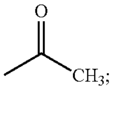

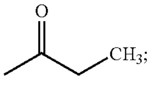

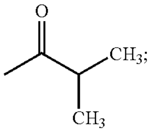

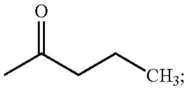

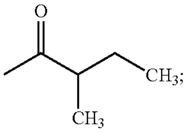
or
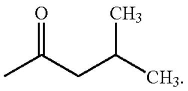

In a preferred embodiment, the invention provides compounds of Formula (II):

(II)

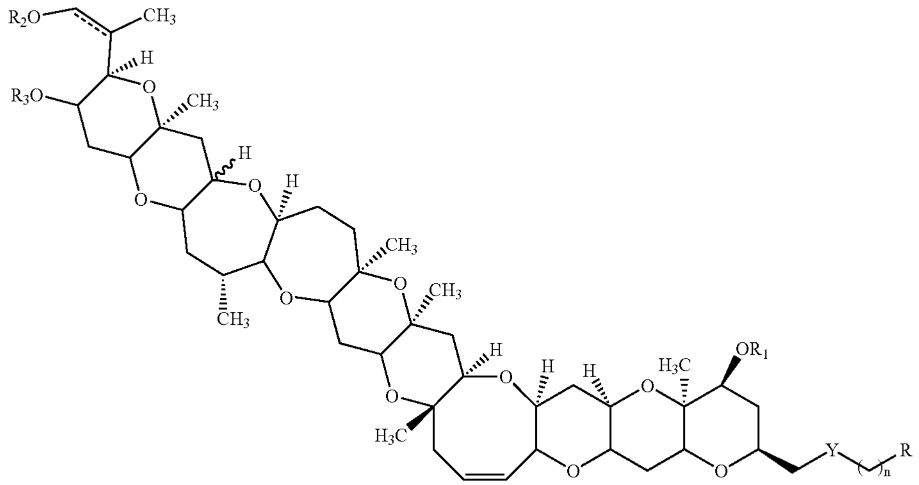

wherein

A is

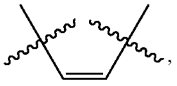

or

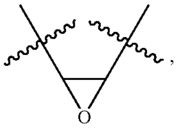

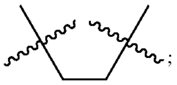

R is $C_1$-$C_6$ alkyl, $C_2$-$C_6$ alkenyl, $C_1$-$C_6$ alkyl esters, $C_2$-$C_6$ alkenyl esters, amines, amides, aryl esters, cycloalkyl esters, cycloalkenyl esters, purines, pyrimidines, heterocycle, or heteroaryl;

$R_1$ is H or $—COCH_3$; and $R_2$ and $R_3$ at each occurrence are independently $—CH_2COCH_3$, $—CH_2COCH_2CH_3$, $—CH_2COCH(CH_3)_2$, $—CH_2COCH_2CH_2CH_3$, $—CH_2COCH(CH_3)CH_2CH_3$, or $—CH_2COCH_2CH(CH_3)_2$, or $OR_2$ and $OR_3$ can be taken together to form a six membered ring of the formula (Ia)

(Ia)

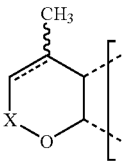

wherein X is C═O or $CH(CH_3)$;

wherein the bracketed-dashed bonds indicate attachment to backbone;

Y is CH═CH, C═O, or $CH_2$; and n is 1 or 0; and with the proviso that when $OR_2$ and $OR_3$ are taken together to form a ring of the formula (Ia), wherein X is C═O and the double bond is present; when A is

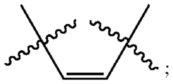

and when n is 1, R is not:

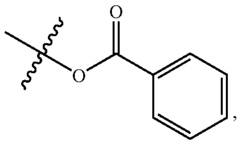

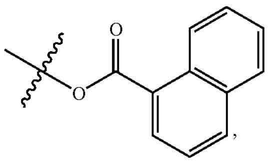

or

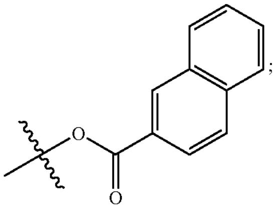

or a pharmaceutically acceptable salt, solvate, hydrate, complex, or combination thereof.

In a further preferred embodiment, the compound of Formula (I) is:

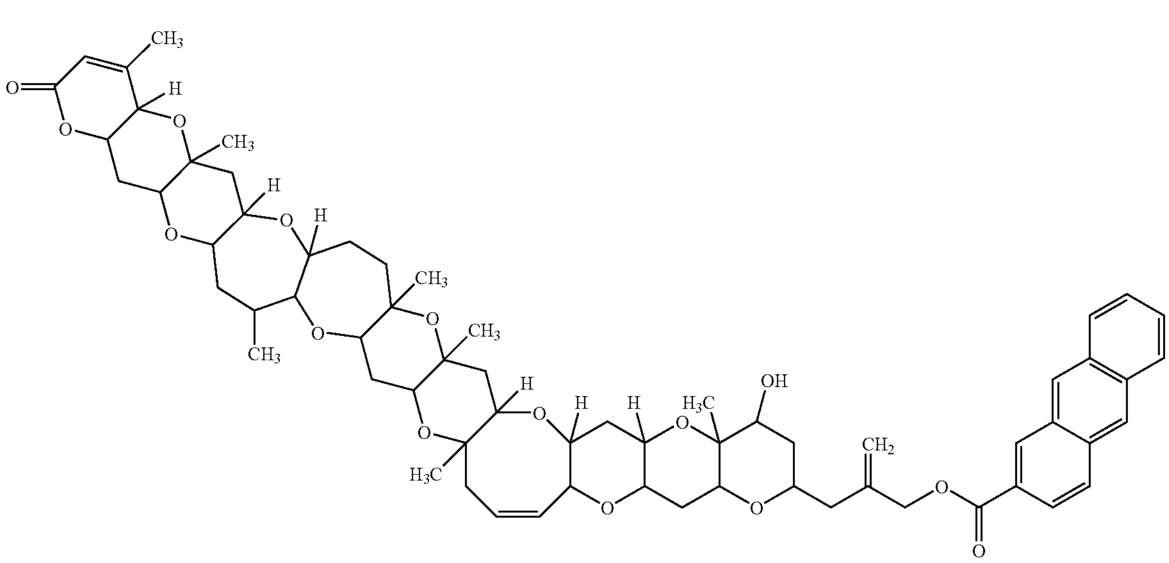
In one aspect of this preferred embodiment, the compound of Formula (I) is:
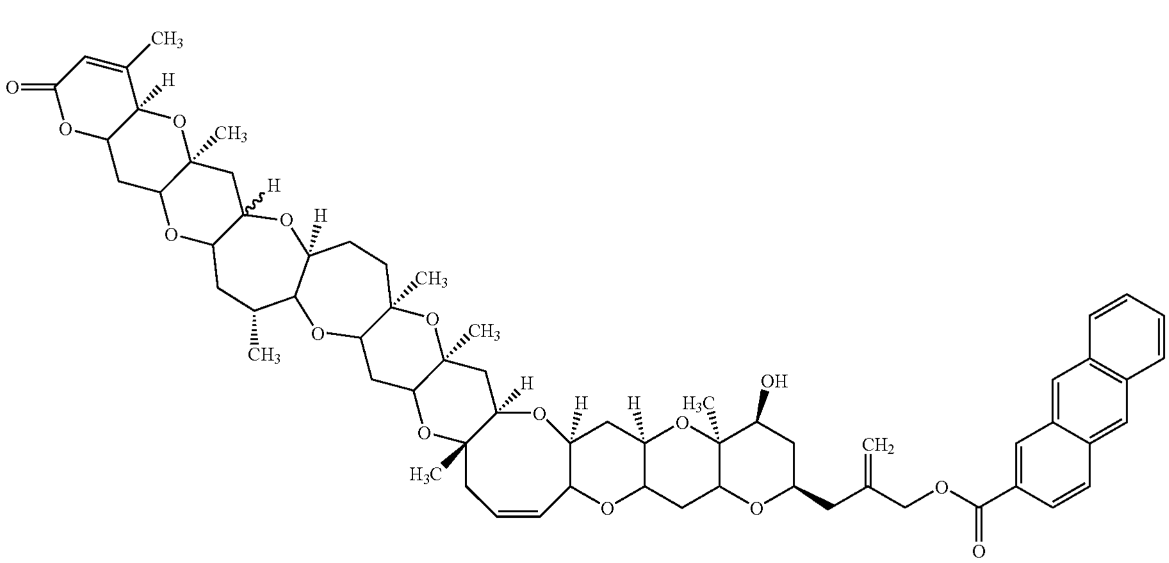

In a further preferred embodiment, the compound of Formula (I) is:
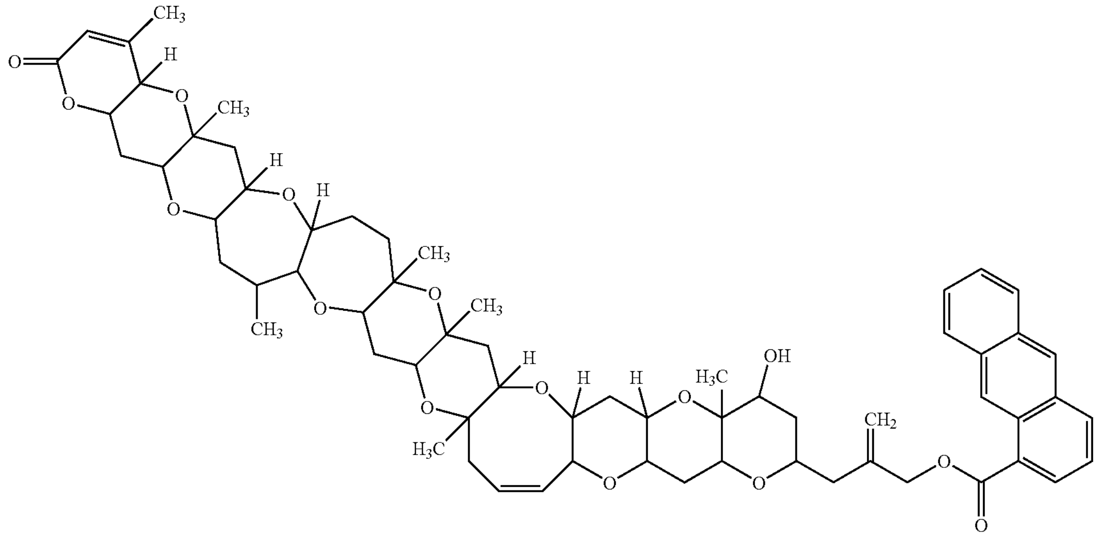
In one aspect of this preferred embodiment, the compound of Formula (I) is:
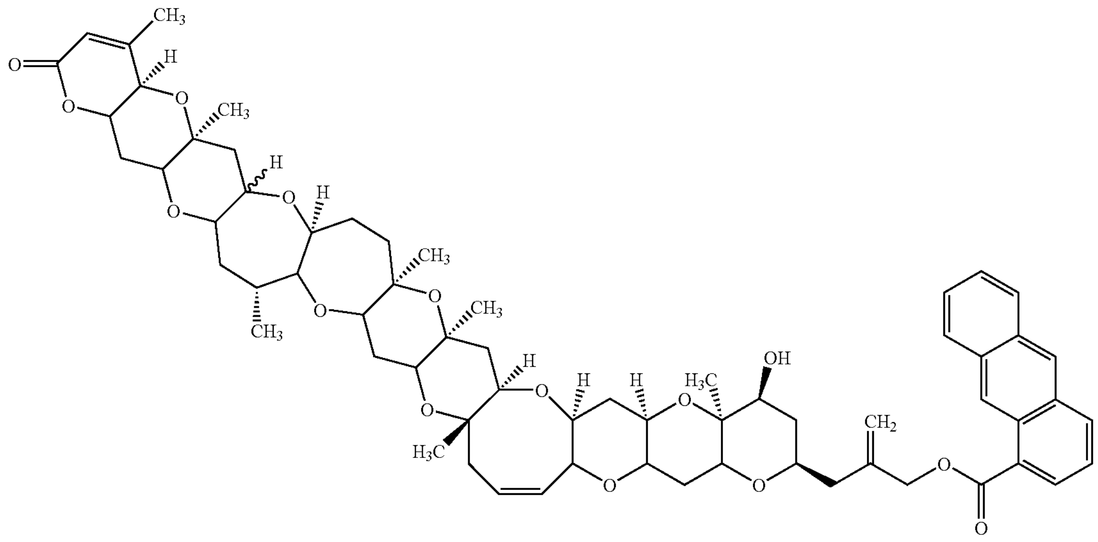

In a further preferred embodiment, the compound of Formula (I) is:
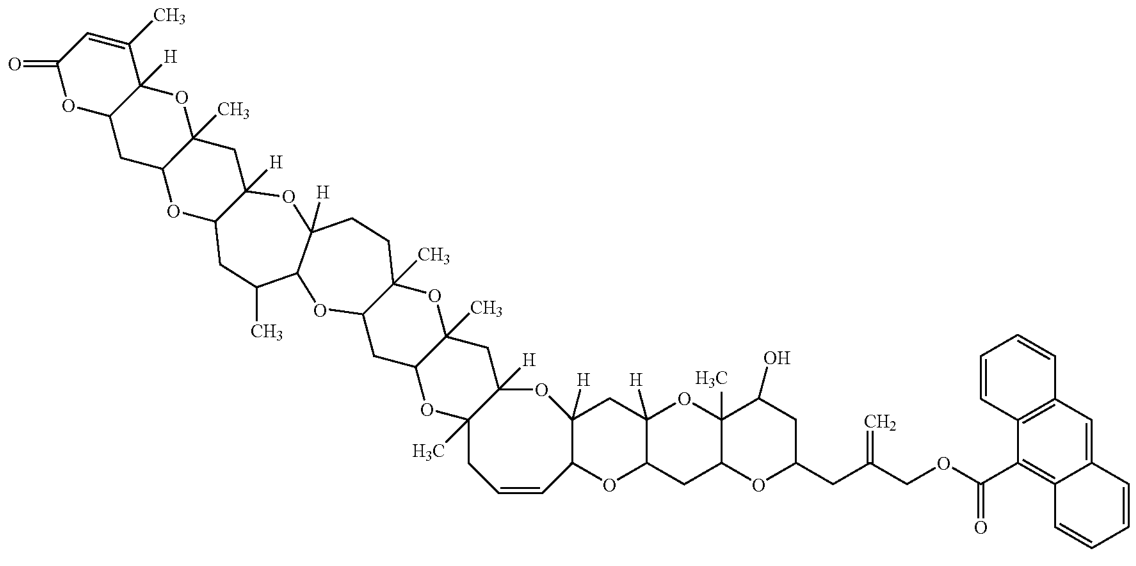
In one aspect of this preferred embodiment, the compound of Formula (I) is:
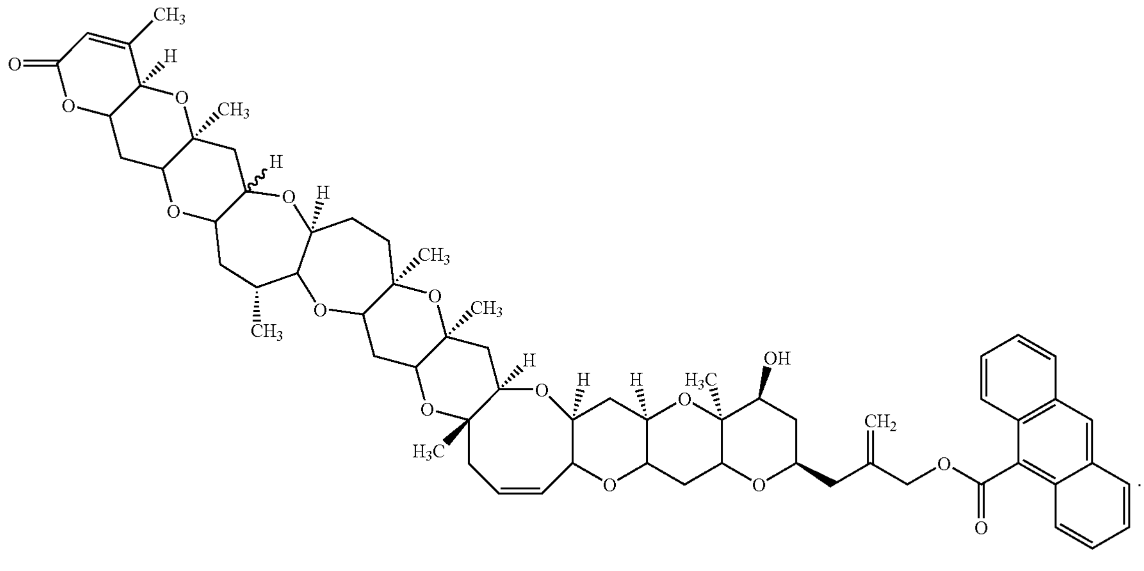
.

The invention also relates to compounds, or pharmaceutically acceptable salts, solvates, hydrates, complexes, or combination thereof, of Formula (III):

(III)

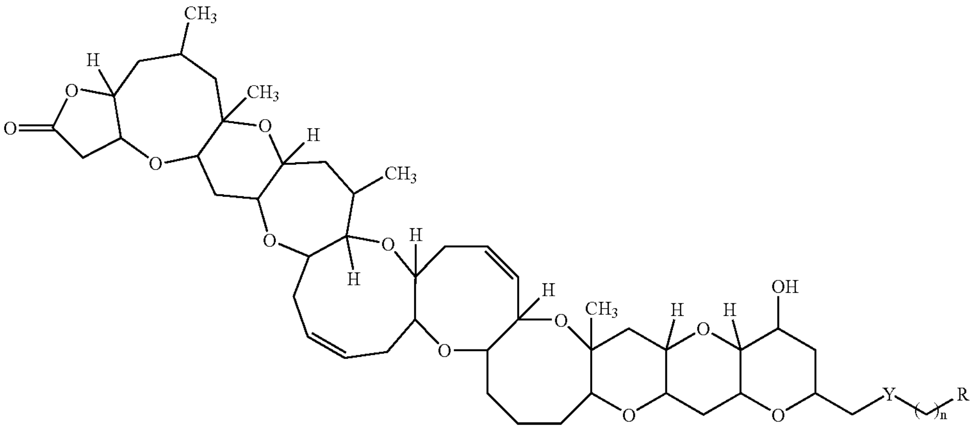

wherein

R is H, OH, halogen, $C_1$-$C_6$ lower alkyl, $C_1$-$C_6$ alkyl esters, $C_2$-$C_6$ alkenyl esters, amino, amido, aldehydo, aryl ester, cycloalkyl ester, cycloalkenyl ester, purinyl, pyrimidinyl, heterocyclyl, aryl, or heteroaryl;

Y is C═O, CH═CH, $CHCH_3$ or $CH_2$; and n is 1 or 0.

In one embodiment of this aspect, the compound of formula (III) is of formula (IV):

(IV)

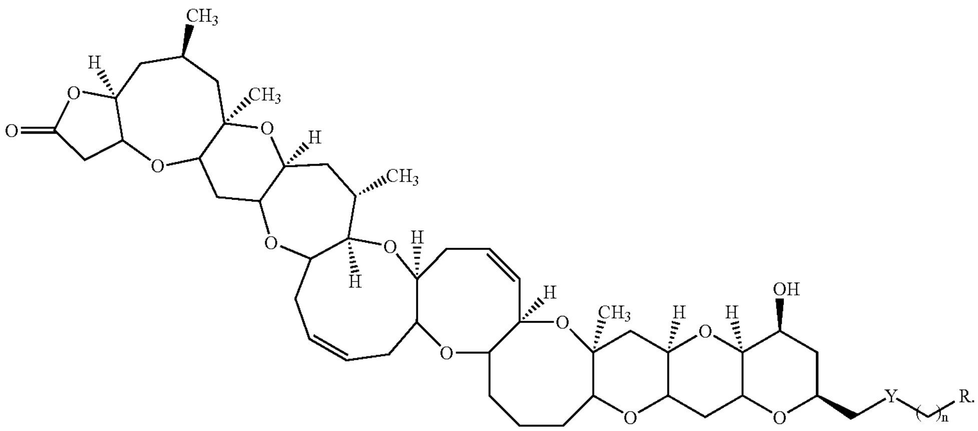

wherein

R is H, OH, halogen, $C_1$-$C_6$ lower alkyl, $C_1$-$C_6$ alkyl esters, $C_2$-$C_6$ alkenyl ester, amino, amido, aldehydo, aryl ester, cycloalkyl ester, cycloalkenyl ester, purinyl, pyrimidinyl, heterocyclyl, aryl, or heteroaryl;

Y is C═O, CH═CH, $CHCH_3$ or $CH_2$; and n is 1 or 0.

In a preferred embodiment the compound of formula (III) is:

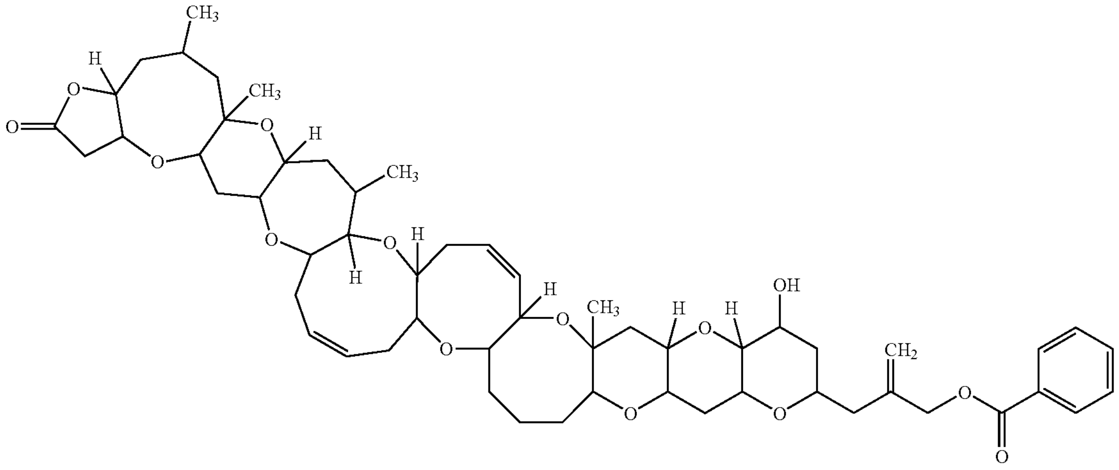
In one aspect of this preferred embodiment, the compound is:
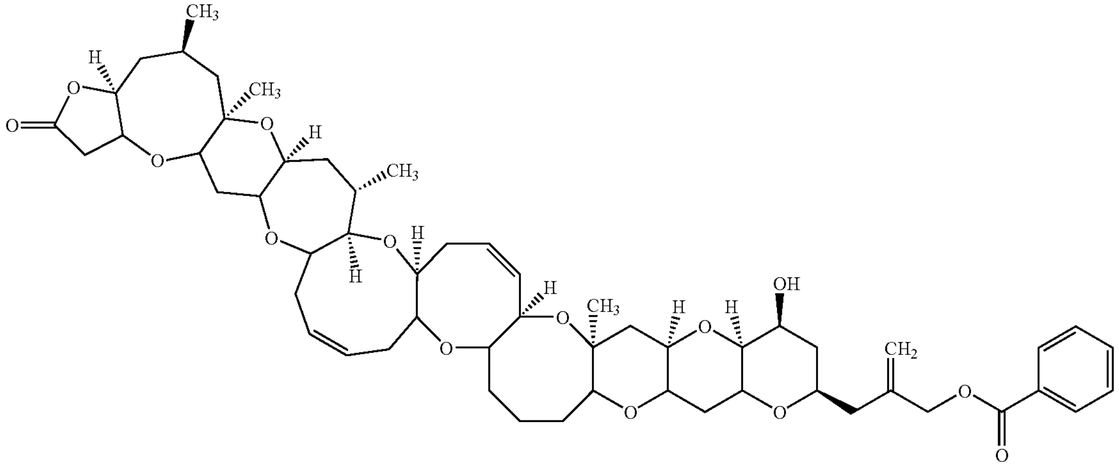
In another preferred embodiment the compound of formula (III) is:
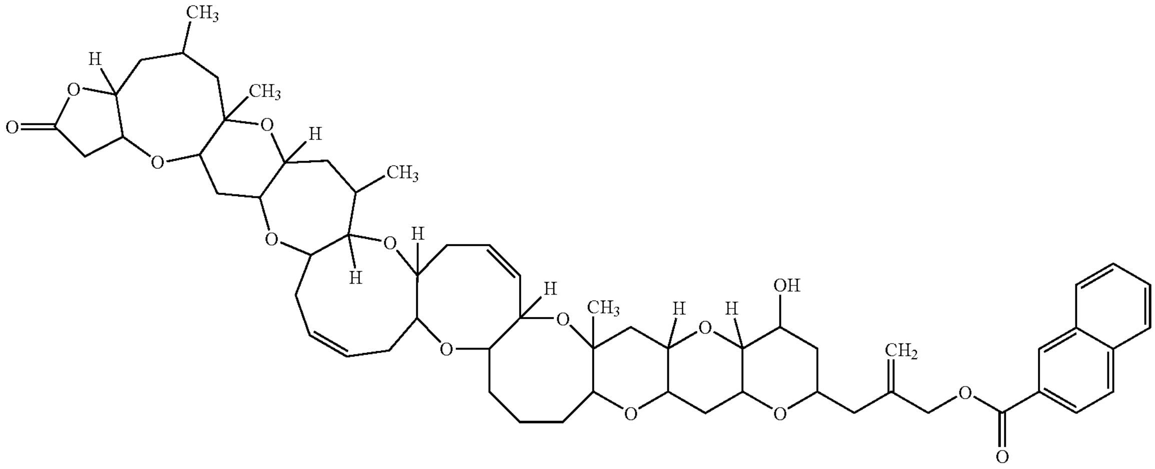

In one aspect of this preferred embodiment, the compound is:
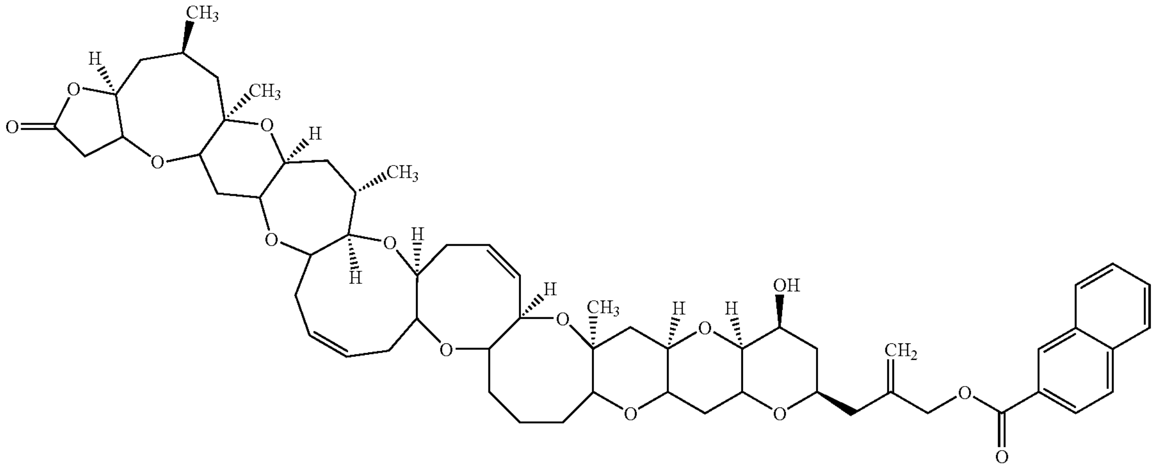
In another preferred embodiment the compound of formula (III) is:
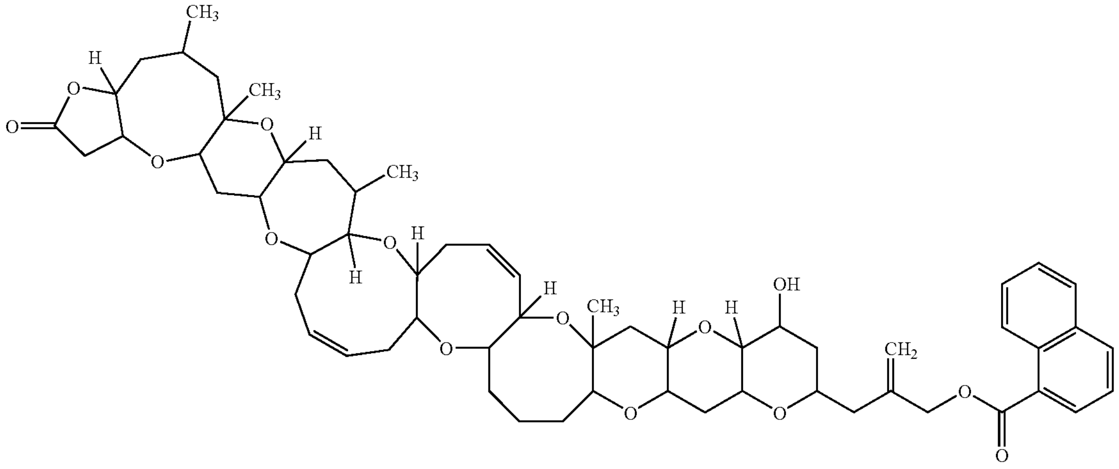
In one aspect of this preferred embodiment, the compound is:
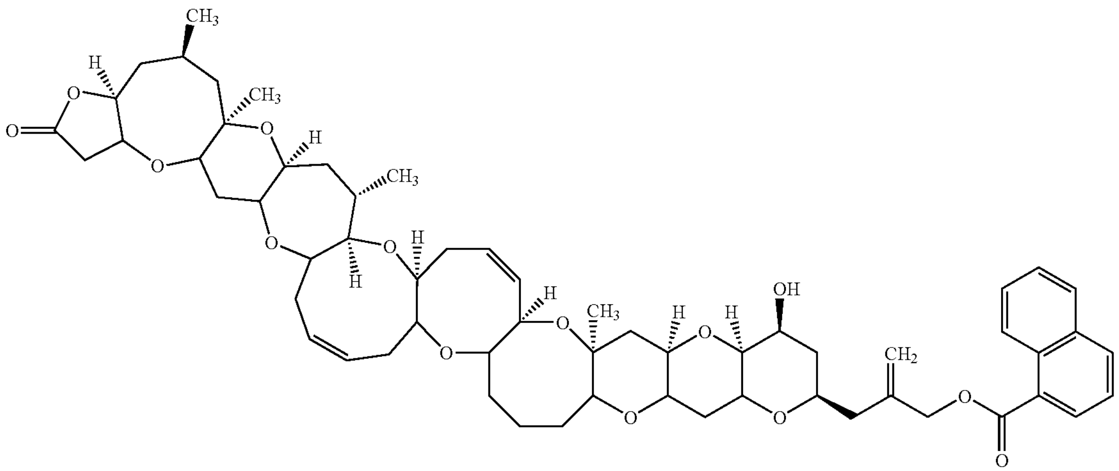

In another preferred embodiment the compound of formula (III) is:
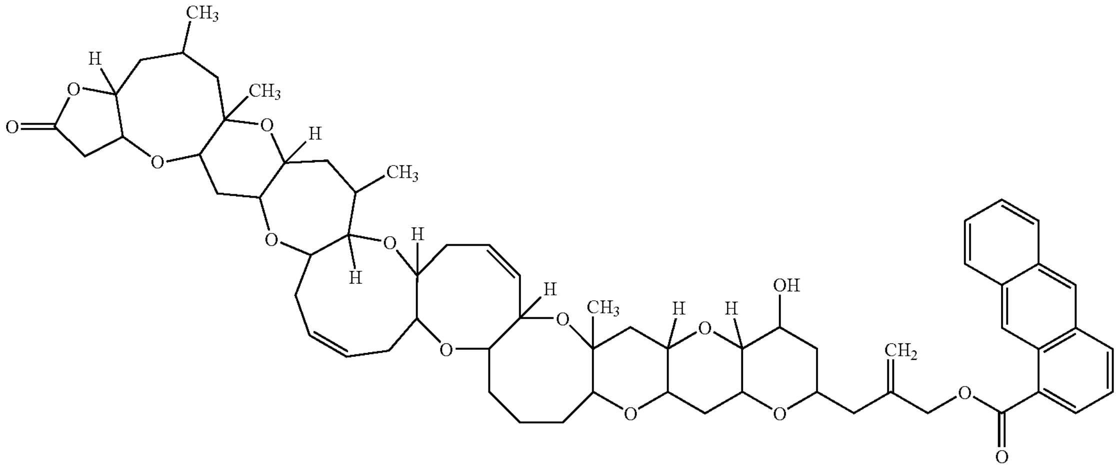
In one aspect of this preferred embodiment, the compound is:
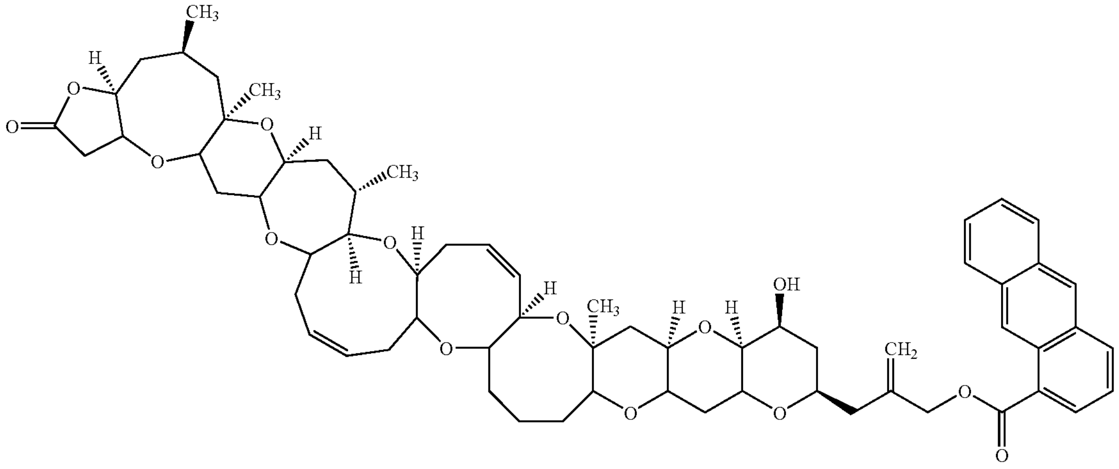
In another preferred embodiment the compound of formula (III) is:
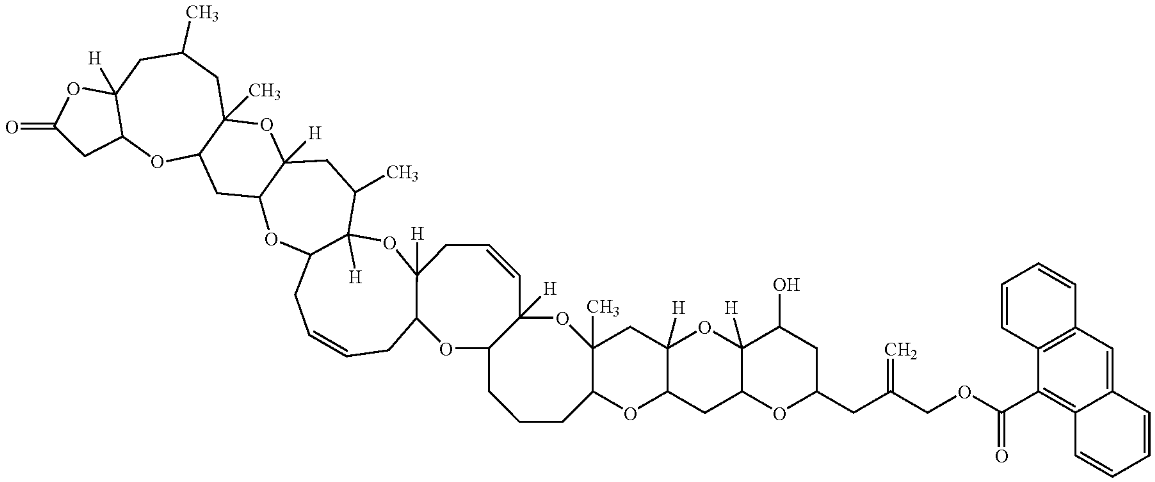

In one aspect of this preferred embodiment, the compound is:
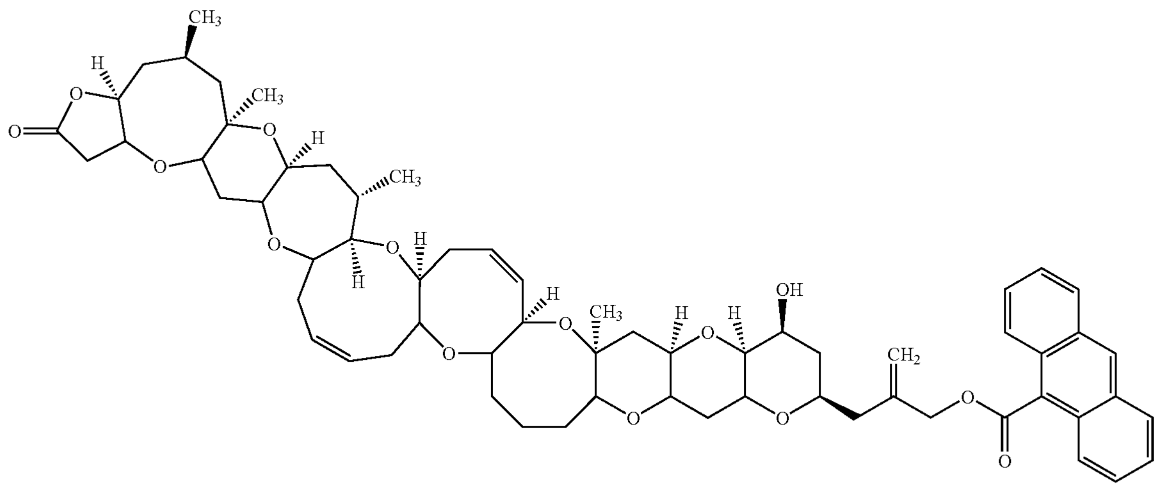
In another preferred embodiment the compound of formula (III) is:
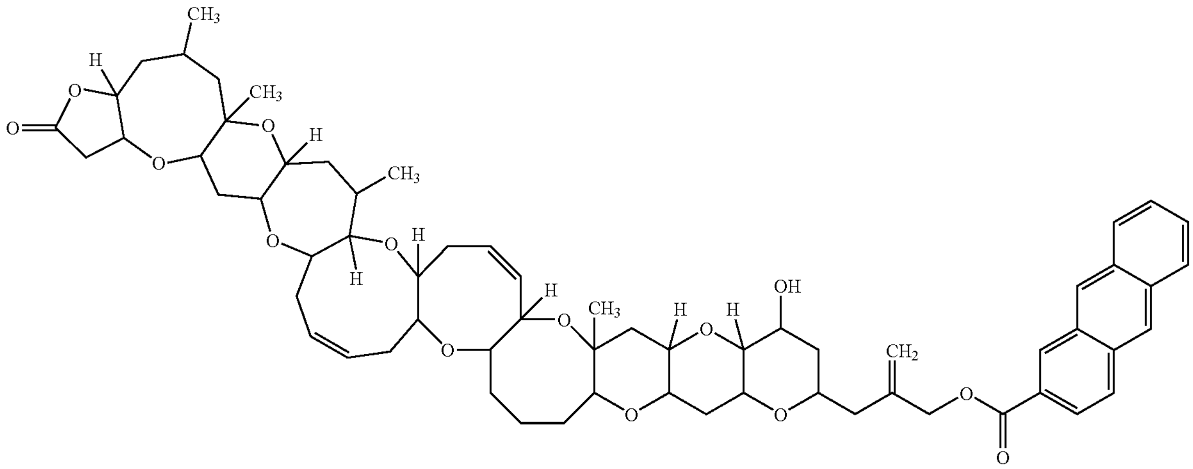
In one aspect of this preferred embodiment, the compound is:
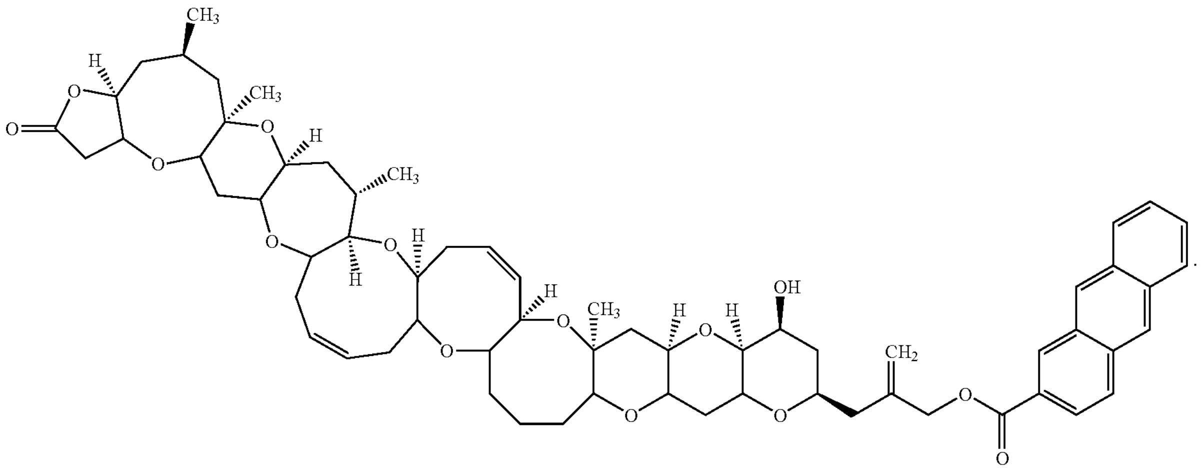

The compounds of Formulas (I)-(IV) may have asymmetric centers and occur as racemates, racemic mixtures and as individual diastereomers, or enantiomers. All isomeric forms are included within the scope of the invention. The invention also encompasses radiolabelled forms of the compounds as well as all physical states, i.e., liquids (oils) and solids (including amorphous forms and crystalline forms), in which the compounds may exist.

In another aspect, the invention relates to pharmaceutical formulations comprising a compound, or pharmaceutically acceptable salt, solvate, hydrate, complex, or combination thereof, of any of Formulas (I), (II), (III), or (IV) and at least one pharmaceutically acceptable carrier, excipient, solvent, adjuvant or diluent.

In a preferred embodiment of this aspect, the pharmaceutical formulation comprises a compound of Formula (II) or (IV).

In another aspect, the invention provides methods for regulating mucus transport comprising administering to a subject, or contacting a cell with, a compound of the invention, or a pharmaceutically acceptable salt, solvate, hydrate, complex, or combination thereof, in an amount effective to regulate mucus transport in the subject or cell.

In another aspect, the invention provides methods for treating conditions or diseases related to, or associated with, decreased mucus transport comprising administering to a subject a compound of the invention or a pharmaceutically acceptable salt, solvate, hydrate, complex, or combination thereof, in an amount effective to treat the condition or disease. This method of treating conditions or diseases associated with decreased mucus transport can help prevent, treat, reduce the severity of, or delay the onset or progression of symptoms and disease states associated with decreased mucus transport. Such conditions or diseases include the non-limiting examples of chronic airway obstruction, asthma, pulmonary disease, pulmonary infection, and cystic fibrosis.

In one embodiment, the method of treatment can be used to treat chronic airway obstruction.

In one embodiment, the method of treatment can be used to treat asthma.

In one embodiment, the method of treatment can be used to treat pulmonary diseases such as emphysema, pulmonary fibrosis, and/or smokers cough.

In one embodment, the method of treatment can be used to treat pulmonary infection, including, but not limited to, pneumonia, or *Pseudomonas*.

In a preferred embodiment, the method of treatment can be used to where the disease is cystic fibrosis.

In another aspect, the invention provides methods for treating the symptoms related to conditions or diseases associated with decrease mucus transport, comprising administering to a subject in need of such treatment, a therapeutically effective amount of a compound of the invention, or a pharmaceutically acceptable salt, solvate, hydrate, complex, or combination thereof.

In another aspect, the invention provides methods for treating conditions or diseases associated with mucociliary dysfunction, comprising administering to a subject in need of such treatment, a therapeutically effective amound of a compound of the invention, or a pharmaceutically acceptable salt, solvate, hydrate, complex, or combination thereof.

In another aspect, the invention provides methods for treating the symptoms related to conditions or diseases associated with mucociliary dysfunction, comprising administering to a subject in need of such treatment, a therapeutically effective amount of a compound of the invention, or a pharmaceutically acceptable salt, solvate, hydrate, complex, or combination thereof.

In another embodiment of this aspect, the method can optionally comprise in combination with the compound of Formula (I)-(IV) or a pharmaceutically acceptable salt, solvate, hydrate, complex, or combination thereof, an effective amount of a compound known to be useful for the treatment of conditions or diseases associated with decreased mucus transport. The methods of the invention can optionally comprise additional therapeutic regimen such as supportive or adjuvant therapy.

In one embodiment of the methods of the invention, the subject is a mammal. In a more preferred embodiment, the mammal is a human.

The methods of the invention employ therapeutically effective amounts: for inhalation, oral, parenteral, sublingual, intranasal, intrathecal, depo, implants, topical, and rectal administration from about 0.1 pg/day to about 100 mg/day. The therapeutically effective amounts will vary according to various parameters including, for example, the route of administration, the distribution of the compound, the metabolism of the compound, the excretion of the compound, the particular therapeutic use, and the physical characteristics of the subject/patient, and are well within the knowledge of those skilled in the art.

In a preferred aspect, the therapeutically effective amounts for oral non-inhalation administration is about 1 mg/day to about 100 mg/day.

In a preferred aspect, the therapeutically effective amounts for parenteral, and depo administration is from about 1 pg/day to about 100 mg/day.

In a preferred aspect, the therapeutically effective amounts for inhalation administration is about 0.1 pg/day to about 1 μg/day.

The invention also includes the use of a compound of Formula (I)-(IV), or a pharmaceutically acceptable salt, solvate, hydrate, complex, or combination thereof for the manufacture of a medicament for use in treating a subject who has, or in preventing a subject from developing, disorders or diseases associated with decreased mucus transport or mucociliary dysfunction, and symptoms associated with those disorders or diseases, and who is in need of such treatment.

In one aspect, this use of a compound of formula (I)-(IV) can be employed where the disease or condition is chronic airway obstruction.

In another aspect, this use of a compound of formula (I)-(IV) can be employed where the disease or condition is asthma.

In another aspect, this use of a compound of formula (I)-(IV) can be employed where the disease or condition is pulmonary disease.

In another aspect, this use of a compound of formula (I)-(IV) can be employed where the disease or condition is pulmonary infection.

In another aspect, this use of a compound of formula (I)-(IV) can be employed where the disease or condition is cystic fibrosis.

In another aspect, compounds of the invention can be employed for treating a industrial related disease or condition caused or exacerbated by inhaling gases, particles of textiles, grit, or other industrial particles or fumes. Specific examples of particles and grit include, for example, iron oxides, silica, talc, carbon, graphite, fibers, wood dust, grain dust, organic solvents and pollutant gases.

In still another aspect, the compounds of the invention can be employed for treating a disease or condition resulting from inhalation of bacterial or other pathogenic particles, e.g., fungal particles. Thus, the invention also encompasses methods of clearing pathogenic particles, such as particles that comprise bacteria, e.g., anthrax or fungus particles.

The invention also includes a container kit including a plurality of containers, each container including one or more unit dose of a compound of formula (I)-(IV), or a pharmaceutically acceptable salt, solvate, hydrate, complex, or combination thereof.

In an embodiment, this container kit includes each container adapted for oral delivery and includes an inhaler, tablet, gel, or capsule.

In an embodiment, this container kit includes each container adapted for parenteral delivery and includes a depot product, syringe, ampoule, or vial.

In an embodiment, this container kit includes each container adapted for topical delivery and includes a patch, medipad, ointment, or cream.

The compounds of formula (I) can form salts when reacted with appropriate acids or bases. Pharmaceutically acceptable salts are generally preferred over the corresponding compounds of formula (I) since they frequently produce compounds that are usually more water soluble, stable and/or more crystalline. Pharmaceutically acceptable salts are any salt which retains the activity of the parent compound and does not impart any deleterious or undesirable effect on the subject to whom it is administered and in the context in which it is administered. Pharmaceutically acceptable salts include acid addition salts of both inorganic and organic acids. Preferred pharmaceutically acceptable salts include salts such as those described by Berge, Bighley, and Monkhouse, J. Pharm. Sci., 1977, 66, 1-19. Such salts may be formed from inorganic and organic acids. Representative examples thereof include maleic, fumaric, benzoic, ascorbic, pamoic, succinic, bismethylenesalicylic, methanesulfonic, ethanedisulfonic, acetic, propionic, tartaric, salicylic, citric, gluconic, aspartic, stearic, palmitic, itaconic, glycolic, p-aminobenzoic, glutamic, benzenesulfonic, hydrochloric, hydrobromic, sulfuric, cyclohexylsulfamic, phosphoric and nitric acids. For other acceptable salts, see *Int. J. Pharm.,* 33, 201-217 (1986). The compounds of formula (I) can also form solvates, hydrates, complexes, or combination thereof.

Methods of the Invention

The compounds of the invention, pharmaceutical formulations comprising said compounds, and pharmaceutically acceptable salts thereof, are useful for treating a subject, preferably a mammal, more preferably a human, suffering from a disease or condition associated with decreased mucus transport, and are useful for helping to prevent or delay the onset of such a disease or condition. The compounds and formulations of the invention are particularly useful for treating, preventing, or slowing the progression of chronic airway obstruction, asthma, pulmonary disease, pulmonary infection, and cystic fibrosis. When treating or preventing a disease and condition associated with decreased mucus transport, and the associated symptoms, the compounds of the invention can either be used individually or in combination, as is best for the subject.

With regard to these diseases and conditions, the term "treating" means that compounds of the invention can be used in subjects, preferably human subjects/patients, with existing condition or disease. The compounds of the invention will not necessarily cure the subject who has the disease but will delay or slow the progression or prevent further progression of the disease thereby giving the individual a more useful life span.

The term "preventing" means that that if the compounds of the invention are administered to those who do not now have the disease, or symptom(s) of the condition, but who would normally develop the disease or be at increased risk for the disease, they will not develop the disease. In addition, "preventing" also includes delaying the development of the disease in an individual who will ultimately develop the disease or would be at risk for the disease due to age, familial history, genetic or chromosomal abnormalities, and/or due to the presence of one or more biological markers for the disease. By delaying the onset of the disease, compounds of the invention can prevent the individual from getting the disease during the period in which the individual would normally have gotten the disease or reduce the rate of development of the disease or some of its effects but for the administration of compounds of the invention up to the time the individual ultimately gets the disease. Preventing also includes administration of the compounds of the invention to those individuals thought to have predisposition for the disease.

In a preferred aspect, the compounds of the invention are useful for slowing the progression of disease symptoms.

In another preferred aspect, the compounds of the invention are useful for preventing the further progression of disease symptoms.

In treating or preventing the above diseases, the compounds of the invention are administered in a therapeutically effective amount. The therapeutically effective amount will vary depending on the particular compound used, the physical characteristics of the subject ot be treated, and the route of administration, as is known to those skilled in the art.

In treating a subject displaying any of the diagnosed above conditions a physician may administer a compound of the invention immediately and continue administration indefinitely, as needed.

Dosage Forms and Amounts

The compounds of the invention can be administered orally, parenterally, (IV, IM, depo-IM, SQ, and depo SQ), sublingually, intranasally, by inhalation, intrathecally, topically, vaginally, or rectally. Dosage forms known to those of skill in the art are suitable for delivery of the compounds of the invention.

Compositions are provided that contain therapeutically effective amounts of the compounds of the invention. The compounds are preferably formulated into suitable pharmaceutical preparations such as aerosols, inhalants, tablets, capsules, or elixirs for oral administration or in sterile solutions or suspensions for parenteral administration. Typically the compounds described above are formulated into pharmaceutical compositions using techniques and procedures well known in the art.

About 0.1 pg to about 100 mg of a compound or mixture of compounds of the invention or a physiologically acceptable salt, solvate, hydrate, complex, ester, or combination thereof, is compounded with a physiologically acceptable vehicle, carrier, excipient, binder, preservative, stabilizer, flavor, etc., in a unit dosage form as called for by accepted pharmaceutical practice. The amount of active substance in those compositions or preparations is such that a suitable dosage in the range indicated is obtained. The compositions are preferably formulated in a unit dosage form, each dosage containing from about 0.1 pg to about 100 mg, preferably about 1 pg to about 1 μg for inhalation administration, preferably about 100 ng to about 1 mg for injection/intravenous administration, or about 1 mg to about 100 mg for oral administration (e.g., tablets, elixirs, capsules, etc.), of the active ingredient. The term "unit dosage from" refers to physically discrete units suitable as unitary dosages for human subjects and other mammals, each unit containing a predetermined quantity of active material calculated to produce the desired therapeutic effect, in association with a suitable pharmaceutical excipient.

To prepare pharmaceutical compositions, one or more compounds of the invention are mixed with a suitable pharmaceutically acceptable carrier. Upon mixing or addition of the compound(s), the resulting mixture may be a solution, suspension, emulsion, or the like. Liposomal suspensions may also be suitable as pharmaceutically acceptable carriers. These may be prepared according to methods known to those skilled in the art. The form of the resulting mixture depends upon a number of factors, including the intended mode of administration and the solubility of the compound in the selected carrier or vehicle. The effective concentration is sufficient for lessening or ameliorating at least one symptom of the disease, disorder, or condition treated and may be empirically determined.

Pharmaceutical carriers or vehicles suitable for administration of the compounds provided herein include any such carriers known to those skilled in the art to be suitable for the particular mode of administration. In addition, the active materials can also be mixed or blended with other active materials that do not impair the desired action, or with materials that supplement the desired action, or have another action. The compounds may be formulated as the sole pharmaceutically active ingredient in the composition or may be combined with other active ingredients.

Where the compounds exhibit insufficient solubility, methods for solubilizing may be used. Such methods are known and include, but are not limited to, using cosolvents such as dimethylsulfoxide (DMSO), using surfactants such as Tween®, and dissolution in aqueous sodium bicarbonate. Derivatives of the compounds, such as salts, solvates, hydrates, complexes, or prodrugs may also be used in formulating effective pharmaceutical compositions.

The concentration of the compound is effective for delivery of an amount upon administration that lessens or ameliorates at least one symptom of the poisoning or disorder for which the compound is administered. Typically, the compositions are formulated for single dosage administration.

The compounds of the invention may be prepared with carriers that protect them against rapid elimination from the body, such as time-release formulations or coatings. Such carriers include controlled release formulations, such as, but not limited to, microencapsulated delivery systems. The active compound is included in the pharmaceutically acceptable carrier in an amount sufficient to exert a therapeutically useful effect in the absence of undesirable side effects on the subject treated. The therapeutically effective concentration may be determined empirically by testing the compounds in known in vitro and in vivo model systems for the treated disorder.

The compounds and compositions of the invention can be enclosed in multiple or single dose containers. The enclosed compounds and compositions can be provided in kits, for example, including component parts that can be assembled for use. For example, a compound inhibitor in lyophilized form and a suitable diluent may be provided as separated components for combination prior to use. A kit may include a compound inhibitor and a second therapeutic agent for coadministration. The inhibitor and second therapeutic agent may be provided as separate component parts. A kit may include a plurality of containers, each container holding one or more unit dose of the compound of the invention. The containers are preferably adapted for the desired mode of administration, including, but not limited to tablets, gel capsules, sustained-release capsules, and the like for oral administration; depot products, pre-filled syringes, ampoules, vials, and the like for parenteral administration; and patches, medipads, creams, and the like for topical administration.

The concentration of active compound in the drug composition will depend on absorption, route of administration, metabolism, inactivation, and excretion rates of the active compound, the dosage schedule, and amount administered as well as other factors known to those of skill in the art.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

If oral, non-inhalation administration is desired, the compound should be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

Oral compositions will generally include an inert diluent or an edible carrier and may be compressed into tablets or enclosed in gelatin capsules. For the purpose of oral therapeutic administration, the active compound or compounds can be incorporated with excipients and used in the form of tablets, capsules, or troches. Pharmaceutically compatible binding agents and adjuvant materials can be included as part of the composition.

The tablets, pills, capsules, troches, and the like can contain any of the following ingredients or compounds of a similar nature: a binder such as, but not limited to, gum tragacanth, acacia, corn starch, or gelatin; an excipient such as microcrystalline cellulose, starch, or lactose; a disintegrating agent such as, but not limited to, alginic acid and corn starch; a lubricant such as, but not limited to, magnesium stearate; a gildant, such as, but not limited to, colloidal silicon dioxide; a sweetening agent such as sucrose or saccharin; and a flavoring agent such as peppermint, methyl salicylate, or fruit flavoring.

When the dosage unit form is a capsule, it can contain, in addition to material of the above type, a liquid carrier such as a fatty oil. In addition, dosage unit forms can contain various other materials, which modify the physical form of the dosage unit, for example, coatings of sugar and other enteric agents. The compounds can also be administered as a component of an elixir, suspension, syrup, wafer, chewing gum or the like. A syrup may contain, in addition to the active compounds, sucrose as a sweetening agent and certain preservatives, dyes and colorings, and flavors.

The active materials can also be mixed or blended with other active materials that do not impair the desired action, or with materials that supplement the desired action.

Solutions or suspensions used for parenteral, intradermal, subcutaneous, or topical application can include any of the following components: a sterile diluent such as water for injection, saline solution, fixed oil, a naturally occurring vegetable oil such as sesame oil, coconut oil, peanut oil, cottonseed oil, and the like, or a synthetic fatty vehicle such as ethyl oleate, and the like, polyethylene glycol, glycerine, propylene glycol, or other synthetic solvent; antimicrobial agents such as benzyl alcohol and methyl parabens; antioxidants such as ascorbic acid and sodium bisulfite; chelating agents such as ethylenediaminetetraacetic acid (EDTA); buffers such as acetates, citrates, and phosphates; and agents for the adjustment of tonicity such as sodium chloride and dextrose. Parenteral preparations can be enclosed in ampoules, disposable syringes, or multiple dose vials made of glass, plastic, or other suitable material. Buffers, preservatives, antioxidants, and the like can be incorporated as required.

Where administered intravenously, suitable carriers include physiological saline, phosphate buffered saline (PBS), and solutions containing thickening and solubilizing agents such as glucose, polyethylene glycol, polypropyleneglycol, and mixtures thereof. Liposomal suspensions including tissue-targeted liposomes may also be suitable as pharmaceutically acceptable carriers. These may be prepared according to methods known for example, as described in U.S. Pat. No. 4,522,811.

The active compounds may be prepared with carriers that protect the compound against rapid elimination from the body, such as time-release formulations or coatings. Such carriers include controlled release formulations, such as, but not limited to, implants and microencapsulated delivery systems, and biodegradable, biocompatible polymers such as collagen, ethylene vinyl acetate, polyanhydrides, polyglycolic acid, polyorthoesters, polylactic acid, and the like. Methods for preparation of such formulations are known to those skilled in the art.

The compounds of the invention can be administered by inhalation, orally or intranasally, parenterally (IV, IM, depo-IM, SQ, and depo-SQ), sublingually, intrathecally, topically, or rectally. Dosage forms known to those skilled in the art are suitable for delivery of the compounds of the invention.

Compounds of the invention may be administered enterally or parenterally. When administered orally, compounds of the invention can be administered in usual dosage forms for oral administration as is well known to those skilled in the art. These dosage forms include the usual solid unit dosage forms of tablets and capsules as well as liquid dosage forms such as solutions, suspensions, and elixirs. When the solid dosage forms are used, it is preferred that they be of the sustained release type so that the compounds of the invention need to be administered only once or twice daily.

The oral dosage forms are administered to the subject 1, 2, 3, or 4, or as needed, times daily. It is preferred that the compounds of the invention be administered either three or fewer times, more preferably once or twice daily. Hence, it is preferred that the compounds of the invention be administered in oral dosage form. It is preferred that whatever oral dosage form is used, that it be designed so as to protect the compounds of the invention from the acidic environment of the stomach. Enteric coated tablets are well known to those skilled in the art. In addition, capsules filled with small spheres each coated to protect from the acidic stomach, are also well known to those skilled in the art.

In a preferred embodiment, the compounds of the invention are administered in an inhalant form.

As noted above, depending on whether asymmetric carbon atoms are present, the compounds of the invention can be present as mixtures of isomers, as racemates, or in the form of pure isomers.

Salts of compounds are preferably the pharmaceutically acceptable or non-toxic salts of compounds of formula I. For isolation and purification purposes it is also possible to use pharmaceutically unacceptable salts.

Synthesis of Compounds

Various synthetic methodologies can be used to make compounds of the invention; certain of the brevetoxins are suitable starting materials. Suitable methodologies are known in the art. Representative synthetic procedures for preparing compounds of the invention from such starting materials are disclosed in, e.g., Mende, T. J., et al., *Tetr. Lett.,* 1990; 31(37): 5307-5310; Trainer, V. L., et al., *Molec. Pharm.,* 1991; 40(6): 988-994; Keck, G. E., et al., *Tetrahedron Lett.,* 1987, 28:139-142; Alvarez, E., et al., *Chem. Rev.,* 1995, 95:1953-1980; Rein, et al., 1994: (a) *J. Org Chem.,* 59:2107-2113; (b) *J. Org. Chem.* 59:2101-2106. Each of these references is incorporated herein by reference in its entirety. Those skilled in the art will appreciate that minor modifications can be made to the particular procedures to arrive at compounds of the invention.

The following examples serve merely to illustrate the invention and should not be viewed to limit the invention in scope or spirit.

EXAMPLES

General. All solvents used were HPLC grade. Brevetoxins were purified from laboratory cultures of the algae *Karenia brevis* (also called *Ptychodiscus brevis* and *Gymnodinium breve*) by a combination of chloroform/methanol extraction and TLC. Brevetoxin can be isolated and purified from native sources, such as *K. brevis*, or other red tide organisms. Suitable purification methodologies are well known in the art. Preferably, brevetoxins are extracted from *K. brevis* cultures. This algae is available from the Provasoli Guillard National Center for Culture of Marine Phytoplankton, West Boothbay Harbor, Me., as strain number CCMP718. In addition, the synthesis of Brevetoxin B has been reported: *J. Am. Chem. Soc.,* 117, 1171 (K. C. Nicolaou et al., 1995).

Starting materials (PbTx-2, -3, and -9) and products were routinely purified by reversed phase HPLC (85% isocratic methanol) using a Microsorb-MV, C-18 column (5 um, 25-cm bed) and monitored by UV at 215 or 195 nM and/or refractive index. Proton NMR spectra were recorded in CDC13 (CHC13 internal standard) at 400 MHz. Mass spectra were run in either DCI or FAB mode. High-resolution mass spectra were obtained from the mass spectrometry facility at the University of California, Riverside.

Synthesis of Brevetoxin Derivatives

A tenfold excess (relative to PbTx-3) of carbonyl diimidazole and the corresponding acid (benzoic, α-naphthoic or β-naphthoic) were combined under nitrogen, at room temperature, in dry benzene. The solution was stirred for 30 min and then added to PbTx-3 in a 5 ml reaction vial. The reaction vial was sealed and the mixture was stirred overnight at 80° C. The reaction mixture was washed with an equal volume (3×) of saturated sodium bicarbonate, an equal volume (3×) of 10% HCl and evaporated under vacuum. The residue was purified using HPLC.

Benzoyl-PbTx-3 (1). Diagnostic peaks in the 1H NMR include 87.44 (2H, t, J=7.2 Hz), 7.56 (1H, t, J=7.2 Hz), 8.061 (2H, d, J=8.4 Hz), 4.81 (2H, dd, J=5.2 Hz) (C42). The C42 methylene is typically shifted downfield from its position in PbTx-3, and these diastereotopic protons are split into a doublet of doublets in the esters, whereas they appear as a singlet in PbTx-3. DCI MS (NH3): 1002 (M+1). HRMS (FAB): calc'd for CS7H, O, S (MH+), calc'd 1001.5262, found 1001.5287.

α-Naphthoyl-PbTx-3 (2). Diagnostic peaks in the 'H NMR include 88.93 (1H, d, J=8.8 Hz), 8.23 (1H, d, J=8.8 Hz), 8.03 (1H, d, J=8.8 Hz), 7.83 (1H, d, J=8.8 Hz), 7.64 (1H, t, J=8.8 Hz), 7.44 (2H, m), 4.92 (2H, dd, J=5.2 Hz) DCI MS (NH3): 1052 (M+1). HRMS (FAB): calc'd for C6iH, 90.5 (MH+), calc'd 1051.5419, found 1051.5367.

β-Naphthoyl-Pb7x-3 (3). Diagnostic peaks in the 1H NMR include 88.64 (1H, s), 7.95 (3H, m), 7.58 (3H, m) 4.89 (1H, s).

carboxylic acid with a hydrolyzed A-ring lactone. The residue was taken up in THF (1 mL), and a catalytic amount of p-toluenesulfonic acid was added. The mixture was stirred for 1 h and then evaporated in vacuo. The residue was taken up in water (1 mL) and extracted with ethyl acetate (3x2 mL). Evaporation of the solvent in vacuo yielded 3.469 mg (93%) of the crude product. Purification of the residue by HPLC provided 1.019 mg (28%) of 2. IHNMR. DCI MS(NH3): 911 (M+1), 929 (M+NH4), 892 (M−H2O).

Scheme 1

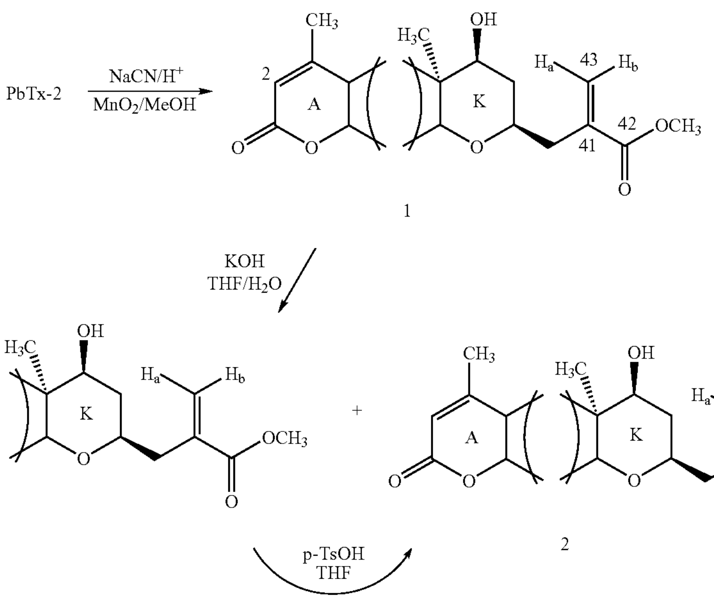

1

2

Example 1

Oxidation of C-42 of PbTx-2 to Ester (1). PbTx-2 (4.8 mg, 5.37 uM) was oxidized with activated $MnO_2$, to the corresponding methyl ester 1, via the cyanohydrin, according to the procedure described by Corey. The reaction mixture was filtered through Celite and concentrated in vacuo. The residue was taken up in water (15 mL) and extracted with ether (3x15 mL). The ether phase was evaporated in vacuo and the residue purified by HPLC to yield 3.624 mg (73%) of the desired product. DCI MS ($NH_3$): 925 (M+1), 942 (M+NH4), 906 (M−H2O).

Example 2

Hydrolysis of Methyl Ester 1 To Provide Carboxylic Acid (2). Methyl ester 1 (3.759 mg, 4.068 uM) was dissolved in 2 mL of THF/$H_2O$ (50:50). An aqueous solution of KOH (0.4 mL, 10 mg/mL) was added, and the reaction mixture was stirred at ambient temperature for 2 days. Water (1 mL) was added and the mixture extracted with ether (3x2 mL). The aqueous phase was acidified with 10% HCl and extracted with ethyl acetate (3x2 mL) and the organic phase evaporated in vacuo. This residue consisted of a mixture of two products. On the basis of NMR data, these two products appear to be the C-42 carboxylic acid with an intact A-ring lactone and the C-42

Example 3

Reduction of the C-2, C-3 Double Bond of PbTx-3 to Provide (3). Following the procedure of Hudlicky, PbTx-3 (4.00 mg, 4.46 uM) and Mg (approximately 200 mg, 99.98% from Timminco metals, Haley, Ontario, Canada) were dried in vacuo over $P_2O_6$ for 18 h. Methanol (3 mL freshly distilled from $CaH_2$) was added and the mixture stirred at room temperature (cooling in an ice bath was required) under nitrogen for 2 h. HCl (10%, 10 mL) was added to dissolve the magnesium methoxide and the remaining magnesium. The reaction mixture was concentrated to approximately 5 mL and extracted with ether (3x15 mL). The ether phase was evaporated in vacuo and the residue purified by HPLC. The isolated material consisted of the desired product with the C-2, C-3 double bond reduced and a second product in which the double bond was reduced and the lactone opened to the methyl ester, as evidenced by mass spectral and NMR data. This mixture was taken up in THF, and a small amount of p-TsOH acid was added. The mixture was stirred for 1 h and then evaporated in vacuo. The residue was taken up in water (1 mL) and extracted with ethyl acetate (3x2 mL). Evaporation in vacuo yielded 3.256 mg (81%) of 3. DCI MS(NH3): 899 (M+1), 916 (M+NH), 880 (M−H2O). HRMS (DCI): calcd for Cr, oH74014 (MH+) 899.5156, found 899.5128.

Example 4

Reduction of the C-2, C-3 Double Bond of PbTx-9 To Provide (4). PbTx-9 (7.49 mg, 8.34 AM) was reduced according to the procedure described for the preparation of 3 to yield 1.645 mg (22%) of 4. The 1H NMR spectrum is shown in the supplementary material. DCI MS(NH3): 901 (M+1), 918 (M+NH4), 882 (M-H, O. HRMS (DCI): calcd for C6pHqg014 (MH+) 901.5313, found 901.5323.

Scheme 2

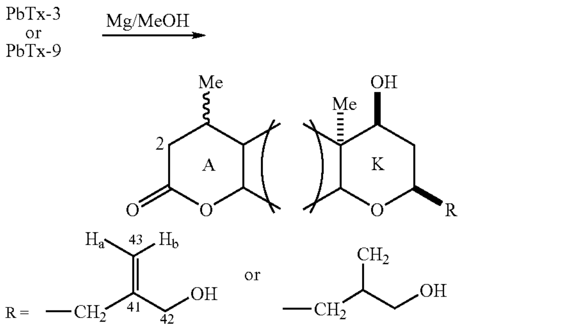

3

4

Scheme 3

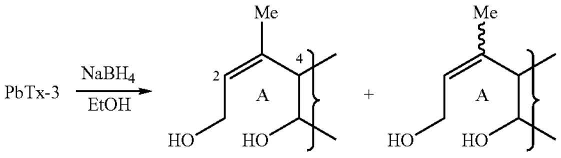

5

6

Scheme 4

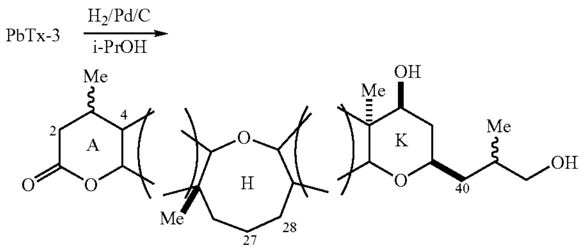

7

Scheme 5

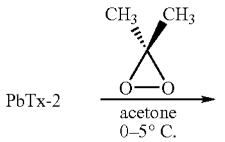

-continued

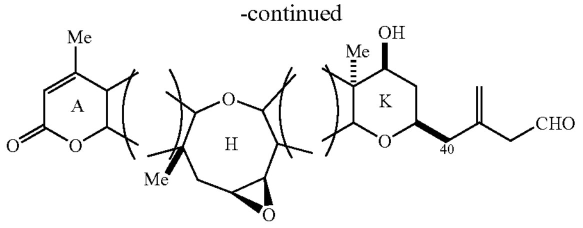

PbTx-6

Example 5

Sodium Borohydride Reduction of PbTx-3 To Form (5) and (6). PbTx-3 (3.451 mg, 3.85 uM) was dissolved in 2.5 mL of EtOH. A large excess of $NaBH_4$ (5 mg) was added in one portion. The reaction mixture was stirred at ambient temperature for 18 h. The excess $NaBH_4$ was decomposed by the careful addition of 10% HCl. The reaction mixture was concentrated in vacuo to 1 mL and extracted with $CH_2Cl_2$ (3×2 mL). The combined organic phases were then evaporated to dryness, and the residue was purified by HPLC. Two peaks were collected from the HPLC. The first peak was the minor product 5, 0.755 mg (22%), and the second peak was the major product 6, 1.042 mg (30%). Compound 5. DCI MS(NH3): 880, 729. FAB MS (m-nitrobenzyl alcohol matrix): 901 (M+1). HRMS (FAB): calcd for C6pHyg014 (MH+) 901.5313, found 901.5324. Compound 6. FAB MS (m-nitrobenzyl alcohol matrix): 903 (M+1), 766, 731. HRMS (FAB): calcd for CrOH78014 (MH+) 903.5470, found 903.5418.

Example 6

Catalytic Reduction of PbTx-3 to Yield (7). PbTx-3 (1.8 mg, 2.00 wM) was dissolved in i-PrOH (1 mL). Acetic acid (50 AL) and a catalytic amount of 10% Pd on activated carbon were added. The reaction mixture was stirred at ambient temperature under an atmosphere of $H_2$ for 24 h. The suspension was filtered through Celite and concentrated in vacuo to provide 0.986 mg (54%) of 7 which was not purified further. DCI MS (NH3): 903 (M+1), 920 (M+NH4), 894 (M-$H_2O$). HRMS (DCI): calcd for CrOH 8014 (MH+) 903.5470, found 903.5444.

Example 7

Epoxidation of the C-27, C-28 Double Bond of PbTx-2 To Provide PbTx-6. Dimethyldioxirane was generated in a distillation apparatus, connected to a dry ice condenser, according to the procedure described by Adam17 for a small-scale preparation. The receiving flask was charged with PbTx-2 (2.33 mg) in 5.0 mL of acetone and was cooled in an ice/salt bath. The reaction was monitored by HPLC. When all of the PbTx-2 was consumed, the acetone was evaporated in vacuo, and the residue taken up in 1.0 mL of methanol and purified by HPLC to provide 2.25 mg (95%) of PbTx-6. DCI MS ($NH_3$): 911 (M+1), 928 (M+$NH_4$), 893 (M-$H_2O$). 1H and 13C NMR were identical to that reported by Shimizu.

Example 8

Airway Merchanics Experimental Protocols

Measurement of Airway Mechanics—Unsedated sheep are restrained in a cart in the prone position with their heads immobilized. After topical anesthesia of the nasal passages with 2% lidocaine solution, a balloon catheter is advanced through one nostril into the lower esophagus. The animals are intubated with a cuffed endotracheal tube through the other nostril using a flexible fiber optic bronchoscope. Pleural pressure is estimated with the esophageal balloon catheter (filled with one ml of air) which is positioned 5-10 cm from the gastroesophageal junction. In this position the end expiratory pleural pressure ranges between −2 and −5 cm $H_2O$. Once the balloon is placed, it is secured so that it remains in position for the duration of the experiment. Lateral pressure in the trachea is measured with a sidehole catheter (inner dimension, 2.5 mm) advanced through and positioned distal to the tip of the endotracheal tube. Transpulmonary pressure, the difference between tracheal and pleural pressure, is measured with a differential pressure transducer catheter system which shows no phase shift between pressure and flow up to a frequency of 9 Hz. For the measurement of pulmonary resistance ($R_L$), the proximal end of the endotracheal tube is connected to a pneumotachograph (Fleisch, Dyna Sciences, Blue Bell, Pa.). The signals of flow and transpulmonary pressure are recorded on an oscilloscope recorder which is linked to a computer for on-line calculation of $R_L$ from transpulmonary pressure, respiratory volume (obtained by digital integration) and flow by the iso-volume technique. Analysis of 5-10 breaths is used for the determination of $R_L$ (Abraham et al., 1994).

Aerosol Delivery Systems—All aerosols are generated using a disposable medical nebulizer (Raindrop®, Puritan Bennett, Lenexa, Kans.) that provide an aerosol with a mass median aerodynamic diameter of 3.2 µm (geometric SD 1.9) as determined by an Andersen cascade impactor. The nebulizer is connected to a dosimeter system, consisting of a solenoid valve and a source of compressed air (20 psi). The output of the nebulizer was directed into a plastic T-piece, one end of which is connected to the inspiratory port of a Harvard respirator. The solenoid valve is activated for one second at the beginning of the inspiratory cycle of the respirator. Aerosols were delivered at a tidal volume of 500 ml and a rate of 20 breaths per minute (Abraham et al., 1994).

Airway Responsiveness—To assess airway responsiveness, we perform cumulative dose response curves to carbachol by measuring $R_L$ immediately after inhalation of buffer and after each consecutive administration of 10 breaths of increasing concentrations of carbachol (0.25, 0.5, 1.0, 2.0 and 4.0% w/v buffered saline). The provocation test is discontinued when $R_L$ increased over 400% from the post-saline value or after the highest carbachol concentration has been administered. Airway responsiveness is estimated by determining the cumulative carbachol dose in breath units (BU) that increases $R_L$ by 400% (PC400) by interpolation from the dose response curve. One breath unit (BU) is defined as 1 breath of an aerosol solution containing 1% wt/vol carbachol (Abraham et al., 1994).

Nasal Airway Resistance—Nasal airway resistance (NAR) is measured with a modified mask rhinomanometry technique. The sheep's head is placed in a plexiglass hood with attachments for a faceplate containing a pneumotachograph to measure flow and two catheter ports to measure the pressure differential between nose and mouth pressure (Abraham et al., 1998).

Tracheal Mucus Velocity—Sheep are nasally intubated with an endotracheal tube 7.5 cm in diameter shortened by 6 cm., after topical anesthesia of the nasal passages with 2% lidocaine solution. The cuff of the tube is placed just below the vocal cords (verified by fluoroscopy) in order to allow for maximal exposure of the tracheal surface area. TMV is measured in vivo by a roentgenographic technique. Between 10 and 20 radiopaque Teflon/bismuth trioxide disks, 1-mm diameter, 0.8-mm thick and 1.8 mg in weight, are insufflated into the trachea via the endotracheal tube. The cephalad-axial velocities of the individual disks are recorded on videotape from a portable image intensifier unit. Individual disk velocities are calculated by measuring the distance traveled by each disk during a 1-min observation period. For each run, the mean value of all individual disk velocities is calculated. A collar containing radiopaque reference markers of known length are worn by the sheep, and used as a standard to correct for magnification effects inherent in the fluoroscopy unit (O'Riordan et al., 1997).

Statistical Analysis—If the data are normally distributed, then parametric statistics are used; if data do not conform to a normal distribution, non-parametric statistics are used. The basic statistical tests include analysis of variance (ANOVA), i.e. one-way ANOVA or two-way ANOVA with repeated measures for multipoint analysis, and unpaired or paired t-test for the appropriate single point analysis. The non-parametric counterparts of these tests are: a) the Mann-Whitney test, which is the counterpart of the unpaired t-test; b) Wilcoxon's signed ranks test, the counterpart of the paired t-test; c) Friedman's Analysis of Variance for related samples, i.e. randomized blocked design; d) the Quade test, also a randomized block design test but for use with small blocks (n≦4); e) the Kruskal-Wallis test, ANOVA for unrelated samples; and f) a non-parametric pairwise comparison, analogous to the parametric Newman-Kuels pairwise test. Where applicable, linear regression analysis is performed by method of least squares, and correlations will be tested for with Spearman's rho test. For all studies, significance is accepted with $p<0.05$ on a two tailed analysis (Conover, 1980).

The invention has been described with reference to various specific and preferred embodiments and techniques. However, it should be understood that many variations and modifications may be made while remaining within the spirit and scope of the invention.

What is claimed is:

1. A method of reducing the severity of or delaying the onset of symptoms associated with cystic fibrosis or asthma in a subject comprising administering to a subject in need of such treatment a therapeutically effective amount of a compound of Formula X, or a pharmaceutically acceptable salt, where Formula X is:

X

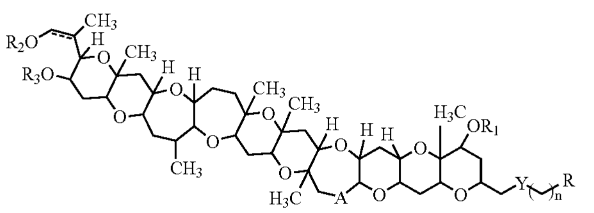

wherein

A is

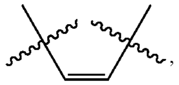,

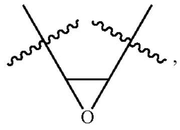, or

-continued

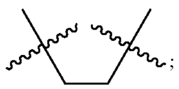;

R is $C_1$-$C_6$ alkyl, $C_2$-$C_6$ alkenyl, $C_1$-$C_6$ alkyl ester, $C_2$-$C_6$ alkenyl ester, amino, amido, aryl ester, cycloalkyl ester, cycloalkenyl ester, purinyl, pyrimidinyl, heterocyclyl, aryl, or heteroaryl;

$R_1$ is H or —(CO)$CH_3$; and $R_2$ and $R_3$ at each occurrence are independently —$CH_2$(CO)$CH_3$, —$CH_2$(CO)$CH_2CH_3$, —$CH_2$(CO)$CH(CH_3)_2$, —$CH_2$(CO)$CH_2CH_2CH_3$, —$CH_2$(CO)$CH(CH_3)CH_2CH_3$, or —$CH_2$(CO)$CH_2CH(CH_3)_2$, or $OR_2$ and $OR_3$ can be taken together to form a six membered ring of the formula (Ia)

(Ia)

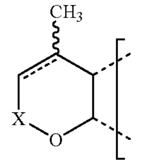

wherein X is CH, C═O, or $CH(CH_3)$;

wherein the bracketed-dashed bonds indicate attachment to backbone;

Y is CH═CH, C═O, $CHCH_3$, or $CH_2$;

n is 1 or 0.

2. A method of treating cystic fibrosis or asthma in a subject comprising administering to a subject in need of such treatment a therapeutically effective amount of a compound of Formula (III), or a pharmaceutically acceptable salt, where Formula (III) is:

(III)

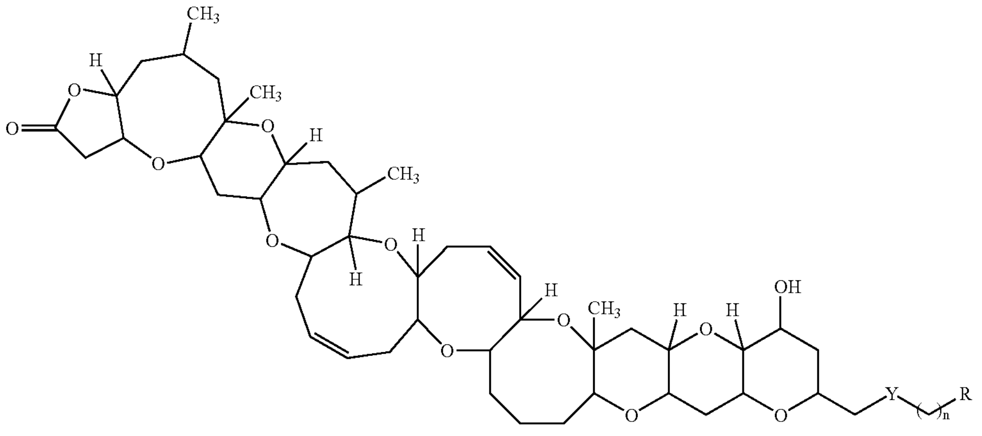

wherein

R is H, OH, halogen, $C_1$-$C_6$ lower alkyl, $C_1$-$C_6$ alkyl ester, $C_2$-$C_6$ alkenyl ester, amino, amido, aldehyde, aryl ester, cycloalkyl ester, cycloalkenyl ester, purinyl, pyrimidinyl, heterocyclyl, aryl, or heteroaryl;

Y is C═O, CH═CH, $CHCH_3$ or $CH_2$; and n is 1 or 0.

3. A method according to claims 1, wherein the therapeutically effective amount is administered in a dosage of between about 0.1 pg to about 100 mg per day.

4. A method according to claim 3, wherein the therapeutically effective amount is a dosage of between about 0.1 pg to about 10 μg per day.

5. A method according to claim 2, wherein the therapeutically effective amount is a dosage of between about 0.1 pg to about 100 mg per day.

* * * * *